(12) United States Patent
Deelman et al.

(10) Patent No.: US 8,198,352 B2
(45) Date of Patent: Jun. 12, 2012

(54) HIGH PURITY MONOALKYLTIN COMPOUNDS AND USES THEREOF

(75) Inventors: Berth Jan Deelman, Kapelle (NL); Jeroen J. M. de Pater, Goes (NL); Evert J. Saman, Kalmthout (BE); Isabelle Tartarin, Lyons (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/992,154

(22) PCT Filed: May 14, 2009

(86) PCT No.: PCT/EP2009/055868
§ 371 (c)(1),
(2), (4) Date: Jan. 28, 2011

(87) PCT Pub. No.: WO2009/138474
PCT Pub. Date: Nov. 19, 2009

(65) Prior Publication Data
US 2011/0166268 A1    Jul. 7, 2011

Related U.S. Application Data

(60) Provisional application No. 61/055,517, filed on May 23, 2008, provisional application No. 61/084,022, filed on Jul. 28, 2008.

(30) Foreign Application Priority Data

May 15, 2008    (EP) .................................... 08103973

(51) Int. Cl.
C08F 7/22    (2006.01)

(52) U.S. Cl. .......................... 524/178; 524/567; 556/81

(58) Field of Classification Search .................. 524/178, 524/567; 556/81
See application file for complete search history.

(56) References Cited

U.S. PATENT DOCUMENTS

| | | | |
|---|---|---|---|
| 2,567,651 A | 9/1951 | Papesch | |
| 2,598,936 A | 6/1952 | Papesch | |
| 2,950,952 A | 8/1960 | Breck | |
| 3,243,394 A | 3/1966 | Dietz | |
| 4,060,512 A | 11/1977 | Scheidl | |
| 4,105,627 A | 8/1978 | Sekiguchi | |
| 4,179,432 A * | 12/1979 | Molt | 524/178 |
| 4,237,043 A * | 12/1980 | Korbanka et al. | 524/180 |
| 4,339,383 A | 7/1982 | Wehner | |
| 4,352,903 A | 10/1982 | Abeler | |
| 4,743,640 A | 5/1988 | Wirth | |
| 5,925,696 A | 7/1999 | Wehner | |
| 6,084,013 A | 7/2000 | Wehner | |
| 6,156,830 A | 12/2000 | Wehner | |
| 6,174,941 B1 | 1/2001 | Wehner | |
| 6,194,494 B1 | 2/2001 | Wehner | |
| 7,592,472 B2 | 9/2009 | Boele | |

FOREIGN PATENT DOCUMENTS

| | | |
|---|---|---|
| DE | 2427853 | 1/1975 |
| DE | 2639086 A1 | 3/1977 |
| DE | 3843581 A1 | 7/1989 |
| DE | 4031818 A1 | 4/1992 |
| DE | 4204887 | 8/1993 |
| DE | 102004037369 A1 | 3/2006 |
| DE | 112005001194 T5 | 4/2007 |
| EP | 0027439 A1 | 4/1981 |
| EP | 0062813 A1 | 10/1982 |
| EP | 0090748 A1 | 10/1983 |
| EP | 0108023 A1 | 5/1984 |
| EP | 0225261 A1 | 6/1987 |
| EP | 0259783 A2 | 3/1988 |
| EP | 0307358 A1 | 3/1989 |
| EP | 0346279 A1 | 12/1989 |
| EP | 0365483 A1 | 4/1990 |
| EP | 0384070 | 8/1990 |
| EP | 0394547 A2 | 10/1990 |
| EP | 0457471 A2 | 11/1991 |
| EP | 0506617 A2 | 9/1992 |
| EP | 0945485 A1 | 9/1999 |
| EP | 1225177 | 7/2002 |
| EP | 1389620 | 2/2004 |
| EP | 1389620 A1 | 2/2004 |
| EP | 1 743 898 * | 1/2007 |
| EP | 1743898 A1 | 1/2007 |
| FR | 1320473 A | 3/1963 |
| FR | 2429806 A | 1/1980 |
| FR | 2459816 A | 1/1981 |
| FR | 2552440 A1 | 3/1985 |
| JP | 57188598 A | 11/1982 |
| NL | 7811090 A | 5/1980 |
| WO | WO93/20135 | 10/1993 |
| WO | WO-9424200 A1 | 10/1994 |
| WO | WO94/26662 | 11/1994 |
| WO | WO-02092686 A1 | 11/2002 |
| WO | WO-2006058789 A1 | 6/2006 |
| WO | WO-2007006783 A1 | 1/2007 |

OTHER PUBLICATIONS

International Application Serial No. PCT/EP2009/055868, International Search Report mailed Sep. 25, 2009, 6 pgs.
Batt, John M., "The Organotin Industry Rises to the HPV Challenge", Applied Organometallic Chemistry, vol. 19, No. 4 (2005), 458-464.
"Strem Chemicals for Research Metals, Inorganics and Organmetallics: Tin (Compounds)", Strem Catalog, No. 20 (2004-2006).

* cited by examiner

Primary Examiner — Ling-Siu Choi
(74) Attorney, Agent, or Firm — Steven D. Boyd

(57) ABSTRACT

The present invention relates to high purity monoalkyltin compounds, more specifically to alkyltin compound compositions containing monoalkyltin as major compound, and minor quantities of di- and/or trialkyltin compounds. The present invention also relates to the preparation processes of such high purity monoalkyltin compounds, as well as to the uses of said monoalkyltin compounds as chlorine-containing polymer-stabilizers, glass coating chemicals and catalysts, as well as articles comprising at least one polymer matrix and a high purity monoalkyltin compound.

20 Claims, No Drawings

HIGH PURITY MONOALKYLTIN COMPOUNDS AND USES THEREOF

FIELD OF THE INVENTION

The present invention relates to high purity monoalkyltin compounds, more specifically to alkyltin compound compositions containing monoalkyltin as major compound, and minor quantities of di- and/or trialkyltin compounds.

The present invention also relates to the preparation processes of such high purity monoalkyltin compounds, as well as to the uses of said monoalkyltin compounds, such as chlorine-containing polymer-stabilisers, glass coating chemicals and catalysts, and the like.

PRIOR ART AND TECHNICAL PROBLEM

Tin-based stabilisers are widely known and used in chlorine-containing polymers and co-polymers, such as for example poly(vinyl chloride) (PVC) polymers and PVC-based copolymers. Such uses of tin-based stabilisers are for example described in the Kirk Othmer "Encyclopedia of Chemical Technology", $4^{th}$ Edition, (1994), vol. 12, Heat Stabilisers, pp. 1071-1091.

These known tin-based stabilisers are used as mixtures of mono-alkyltin with di-alkyltin compounds. For example widely used tin-based compounds in PVC polymers and copolymers are mixtures of mono- and di-methyltin compounds, mono- and di-butyltin compounds or mono- and di-octyltin compounds, such as those sold under the name Thermolite® by Arkema.

However, tri-alkyltin compounds are known to be toxic compounds, and di-alkyltin compounds have recently been classified as toxic compounds. Toxicity of tin compounds is known to be linked to mono-, di- and tri-alkyl tin compound contents, particularly toxicity is increasing from mono-, to di- and to tri-alkyl tin compound contents. Therefore it is nowadays highly relevant to develop mono-alkyltin compounds, with low levels of di- and tri-alkyl tin compounds, in order to avoid toxicity issues.

Attempts to the production of high purity mono-alkyltin chlorides have been conducted, for example through redistribution of tetra-alkyltin and tri-alkyltin compounds with tin tetrachloride followed by fractional distillation: mono-alkyltin chlorides were obtained in relatively pure form but di-alkyltin chlorides were always co-produced in significant quantities rendering these routes less attractive from an industrial perspective.

Recently developed technology as disclosed in EP-A-0 1 225 177 and EP-A-1 743 898 allows the more selective production of mono-alkyltin chlorides without producing significant amount of di- and tri-alkyltin species as by-products. These technologies provide access to high purity monoalkyltin compounds through relatively short purification procedures.

Therefore an objective of the present invention is to provide non-toxic or less toxic tin-based compounds or compositions for stabilising polymers, more specifically chlorine-containing polymers, e.g. PVC polymers and copolymers.

Another objective of the present invention is to provide high purity monoalkyltin compounds, i.e. compositions with a major content of monoalkyltin compound and minor contents, and preferably only traces of, and even more preferably no di- and tri-alkyltin compounds, for use as stabilisers for chlorine-containing polymers, especially PVC polymers, post-chlorinated PVC and copolymers thereof, as well as for uses as a catalyst, or in glass coating compositions.

BRIEF DESCRIPTION OF THE INVENTION

The inventors have now discovered that high purity monoalkyltin trihalides can be converted to other mono-alkyltin derivatives that are of interest for several existing applications. The technology developed thus provides high purity mono-alkyltin compounds on an industrial scale as more benign alternatives to currently applied mixtures of mono- and di-alkyltin compounds.

The inventors have also discovered that high purity mono-alkyltin compounds, when used for example as stabilisers for chlorine-containing polymers and copolymers, provide to said polymers and copolymers remarkable and unexpected stability properties, more specifically thermal properties, long term colorhold retention properties, transparency properties (specifically for polymer films of variable thickness), among others.

DETAILED DESCRIPTION OF THE INVENTION

In a first aspect, the present invention relates to a composition comprising:
  from 85 wt % to 99.999 wt %, preferably from 90 wt % to 99.999 wt %, more preferably from 95 wt % to 99.99 wt %, still more preferably from 97 wt % to 99.99 wt % (limits included) of at least one monoalkyltin compound of formula $RSn(T)_3$, in which R is linear, branched or cyclic $C_1$-$C_{20}$ alkyl, preferably $C_1$-$C_{10}$ alkyl, and T is a ligand;
  from 0.001 wt % to 10 wt %, preferably from 0.001 wt % to 1 wt %, more preferably from 0.01 wt % to 0.5 wt %, most preferably from 0.01 wt % to 0.1 wt %, of at least one di-alkyltin compound of formula $R_2Sn(T)_2$, in which R and T are as defined above;
  from 0.001 wt % to 5 wt %, preferably from 0.005 wt % to 1 wt %, more preferably from 0.01 wt % to 0.5 wt %, most preferably from 0.01 wt % to 0.1 wt %, of at least one tri-alkyltin compound of formula $R_3Sn(T)$, in which R and T are as defined above; and
  from 0 wt % to 5 wt %, more preferably from 0 wt % to 1 wt %, still more preferably from 0 wt % to 0.2 wt % of one or more impurities.

According to another aspect, the composition of the present invention comprises a weight ratio of (mono-alkyltin compound)/(di-alkyltin compound) of not less than 90/10, preferably of not less than 95/5, most preferably of not less than 97/3.

According to still another preferred aspect, the composition of the present invention comprises a weight ratio of (mono-alkyltin compound)/(tri-alkyltin compound) of not less than 99/1, preferably of not less than 99.5/0.5, more preferably of not less than 99.7/0.3.

Still according to another aspect, the composition of the present invention comprises an amount of tri-alkyltin compound(s) of less than 1 wt %, preferably of less than 0.5 wt %, most preferably the composition comprises traces, expressed as parts per million (ppm), and even parts per billion (ppb) of tri-alkyltin compound(s).

Impurities that may be found in the composition of the present invention are any and all impurities that may be found as residues (or traces) from the preparation process of the composition, such as ligand precursors, ligand precursor-hydrolysed by-products, tin halides, solvents, alkenes, alkyl halides, catalysts or catalyst components, decomposed catalysts or catalyst components, water, neutralization salts, and the like.

In the composition of the present invention, R is a linear, branched or cyclic alkyl radical having from 1 to 20 ($C_1$-$C_{20}$ alkyl), preferably from 1 to 10 carbon atoms ($C_1$-$C_{10}$ alkyl), and preferably R is methyl, ethyl, propyl, butyl, pentyl, hexyl, heptyl, octyl, nonyl, decyl, cyclopentyl, cyclohexyl, cycloheptyl. The R radical may also comprise one or more unsaturations in the form of double and/or triple bond(s), and in such cases R may be chosen from among propenyl, butenyl, butadienyl, pentenyl, octenyl, octadienyl, cyclohexenyl, phenyl, and the like.

According to a preferred embodiment, R is chosen from among ethyl, n-propyl, iso-propyl, n-butyl, iso-butyl, n-pentyl, n-hexyl, n-heptyl, n-octyl, 2-ethylhexyl, iso-octyl, and decyl. More preferably R is methyl, n-butyl, 2-ethylhexyl, n-octyl, or n-decyl.

As regards the ligand T, it is any ligand known in the art, for example as disclosed in EP 0 010 008 or EP 0 501 780. More preferably, T is a ligand the precursor of which being H-T. H-T compounds may advantageously be chosen from among H—$SCH_2CH_2OH$, H—$SCH_2$—$CH(OH)$—$CH_3$, H—$SCH_2COOR^1$, H—$SCH_2CH_2O$—$COR^2$, H—$SR^2$, H—OH, H—$OOCR^2$, and H—$OOCR^3$—$COOR^2$, wherein $R^1$ represents $C_1$-$C_{12}$ alkyl, $R^2$ represents $C_6$-$C_{18}$ alkyl, aryl or alkaryl, $R^3$ represents —CH=CH—; or —$CH_2$—$R^4$—$CH_2$—, with $R^4$ representing $C_2$-$C_6$ alkylene.

According to a preferred embodiment, T is chosen from among thioglycolate esters, 2-ethylhexylthioglycolate esters, iso-octylthioglycolates, iso-butylthioglycolates, thioglycolate itself, hydroxyl, carboxylates, maleates, diketonates, alcoholates, more preferably T is 2-ethylhexylmercaptoacetate (EHMA).

In the formula $RSn(T)_3$, each T may be identical or different from the others. According to still a preferred embodiment, all three ligands T are identical.

Preferred compounds of formula $RSn(T)_3$ are RSn[tris(2-ethylhexyl-mercaptoacetate)], and among them the preferred ones are chosen from among monomethyltin[tris(2-ethylhexylmercaptoacetate)], mono-n-butyltin[tris(2-ethylhexylmercaptoacetate)], mono-n-octyl[tris(2-ethylhexylmercaptoacetate)], and mixtures thereof. Advantageously, the composition of the present invention comprises mono-n-octyl[tris(2-ethylhexylmercaptoacetate)] as major compound.

According to another aspect, the present invention relates to the process of preparation of the above-described tin-based compositions. High purity monoalkyltin-based compounds of formula $RSn(T)_3$, in which R and T are as defined above, are advantageously prepared from the corresponding monoalkyltin trihalides of formula $RSn(Hal)_3$, in which R is as defined above and Hal is chosen from chlorine, bromine and iodine.

Some monoalkyltin trihalide preparations are already known form the prior art, and among them may be cited distillation of monoalkyltin halides from thermal redistribution mixtures containing mono-, di- and tri-alkylhalides. However, on an industrial point of view, distillation is less preferred when co-produced di- and/or tri-alkyltin compounds are not desired, since extensive distillation fractionation is often necessary to yield mono-alkyltin compounds of high purity, and particularly with a weight ratio of (mono-alkyltin) to (di-alkyltin) compounds greater than 90/10, preferably greater than 95/5, more preferably greater than 97/3.

Catalytic platinum-catalysed redistribution of di-alkyltin dihalides with tin tetrachloride is one of the few general methods for the selective production of mono-alkyltin species from higher alkyltins, but tin(II) halide is however formed as a by-product in substantial amounts. The only other selective preparation process leading to monoalkyltin halides involves palladium-catalysed hydrostannylation of 1-alkenes in the presence of tin(II) dihalide and hydrogen halide and is disclosed in patent application WO 07/006,783.

Other known methods for the selective production of mono-alkyltin trihalides generally suffer from poor yields due to the use of harsh reaction conditions, are limited to $RSn(Hal)_3$ compounds, wherein R represents methyl or unsaturated hydrocarbyl, or use non-economical amounts of catalyst or alkylating agent (EP-A-1 225 177; S. H. L. Thoonen, *J. Organomet. Chem.*, 689, (2004), 2145-2157).

Selectively produced mono-alkyltin trihalides have been found to be easily converted to mono-alkyltin compounds of formula $RSn(T)_3$ by reacting mono-alkyltin halides $RSn(Hal)_3$ with a compound of formula H-T in the presence of a suitable base. Alternatively compounds of formula $RSn(T)_3$ can be prepared by reaction of $RSn(Hal)_3$ to alkylstannoic acid RSn(O)OH using a hydroxide base, followed by contacting the alkylstannoic acid with a compound of formula H-T under elimination of water.

The present invention therefore provides a very easy, cost-effective and industrial process of preparation of the above-described and claimed composition, i.e. of mono-alkyltin compounds of high purity of formula $RSn(T)_3$, wherein R and T are as defined above, said process comprising:
  α) hydrostannylation of a 1-alkene to the corresponding mono-alkyltin trihalide $RSn(Hal)_3$ in the presence of a transition metal catalyst, tin(II) dihalide and hydrogen halide; and
  β) converting the mono-alkyltin trihalide $RSn(Hal)_3$ to $RSn(T)_3$ by contacting the mono-alkyltin trihalide $RSn(Hal)_3$ with a compound of formula H-T in the presence of a suitable base or, alternatively, by reacting $RSn(Hal)_3$ to alkylstannoic acid RSn(O)OH using a hydroxide base followed by contacting the alkylstannoic acid with a compound of formula H-T under elimination of water.

More precisely, the process of preparation of mono-alkyltin compounds of high purity of formula $RSn(T)_3$, wherein R and T are as defined above, comprises the steps of:
  a) preparing a solution of stannous halide $SnHal_2$ in a solvent, together with a transition metal-based catalyst;
  b) reacting the obtained solution with a molar excess (1.5 to 2 molar equivalents relative to the stannous halide) of the corresponding alkene or cycloalkene precursor of the R radical, at a temperature ranging between room temperature to 200° C., in the presence of hydrogen halide (H-Hal) and optionally metallic tin (Sn);
  c) optionally removing the solvent of the reaction medium, for example stripping or vacuum-distillation of the solvent;
  d) optionally filtering the crude reaction medium;
  e) adding a 2- to 5-fold molar excess (relative to the obtained monoalkyltin trihalide) of H-T, and water, under stirring;
  f) neutralising the reaction medium, for example with alkali or alkaline-earth hydroxide, e.g. sodium hydroxide;
  g) separating the water layer from the organic layer; and
  h) removing the solvent from the organic layer, and optionally filtering to recover $RSn(T)_3$ of high purity.

In a specific embodiment of the above process, Hal is chloride. This means that the stannous halide is $SnCl_2$ and hydrogen halide is HCl. Stannous bromide and stannous iodide may also be used.

As regards the alkene or cycloalkene precursor (sometimes called olefin) of the R radical, it can be described, by way of example, with the following formula:

and the reaction route as follows (eq 1):

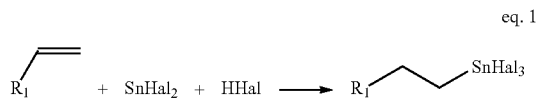

eq. 1 in which $R_1$ is H or is defined as an alkyl (linear or branched or substituted), having from 1 to 18 carbon atoms.

The alkene, but also cycloalkene, has advantageously from 2 to 20 carbon atoms. In a specific embodiment the alkene also can be described as $R_1(R_2)C=C(R_3)(R_4)$ with $R_1$-$R_4$ being any alkyl group (branched or linear or substituted) or hydrogen, $R_1$, $R_2$, $R_3$ and/or $R_4$ being optionally linked to any of the other R groups, for example $R_1$ or $R_2$ being linked to $R_3$ or $R_4$, or $R_1$ being linked to $R_2$, and the number of carbon atoms in $R_1$-$R_4$ ranging from 0 to 18.

The olefin can contain functions and/or substituents. Advantageously this hydrocarbon has 4 to 8 carbon atoms. Especially 1-butene and 1-octene are relevant to produce industrially important organotins.

As regards stannous halide, it can be $SnHal_2$ or any precursor. Mention may be made, by way of examples, of $Sn/SnHal_4$ blends and HHal/Sn. The precursor also relates to $SnHal_2/Sn/SnHal_4$ blends. The stannous halide is preferably anhydrous but also their aqua complexes can be used. The stannous halide $SnHal_2$ can be produced in situ. According to a specific embodiment, $SnHal_2$ can be partly or totally replaced by an $Sn/SnHal_4$ blend (1/1 ratio) producing $SnHal_2$ in situ.

As regards the hydrogen halide, it can be the hydrogen halide itself as gas or solution in a solvent or any precursor or any blend thereof. The precursor can be $[HN(alkyl)_3]Hal$, another ammonium salt or other Lewis base adduct of hydrogen halide. When used as gas the hydrogen halide may be diluted with another gas. In a preferred embodiment of the invention the hydrogen halide can be HCl or $[HN(C_2H_5)_3]Cl$. In another preferred embodiment, Hal is chloride, the stannous halide is $SnCl_2$ and hydrogen halide is HCl.

As regards the catalyst, in its broadest form the catalyst is a transition metal-based catalyst, such as a palladium-based catalyst, supported or not, as commonly used in the art. Examples of such catalysts are widely described in WO 2007/006783. Preferably, the complex is $M(PPh_3)_4$, wherein M is chosen form among Pt, Pd and/or Ni, preferably M is Pd.

Support for the catalyst may be of any type known in the art and is preferably carbon.

As regards the solvent, in general organic, aprotic or even protic solvents are preferred, especially aromatic solvents, chloroaromatic solvents, alkanes, ethers and alcohols. In particular tetrahydrofuran (THF), ethanol and 1,2-dimethoxyethane (DME) are suitable solvents.

As regards the operating conditions and the proportions, the reaction is made continuously or in batch. The batch process is preferred. Temperature can be, by way of example, from ambient to 200° C. A range from 20° C. to 130° C. is advantageous, preferably from 20° C. to the boiling point of the solvent.

As regards the pressure, no pressure is necessary except to maintain the alkene, when it has a low boiling point, and hydrogen halide in the reaction medium. However, to speed up the reaction higher pressures may be advantageous.

Preferred reaction times range from a few seconds to 48 hours. The molar ratio of olefin to $SnHal_2$ falls within the range 0.1/1 to 200/1, more advantageously 1/1 to 100/1. The molar ratio of HHal to $SnHal_2$ falls within the range 0.01/1 to 100/1.

The catalyst loading (molar percentage of M) based on the number of moles of $SnHal_2$ can be 0.001 to 5%, more preferred 0.1 to 1.5%. Should a solvent be used, any proportion is convenient.

The reaction is carried out in any usual apparatus. The reaction can be checked by taking samples and conventional analysis. According to an embodiment, the monoalkyltin trihalides can be separated from the reaction medium by any means such as, by way of examples, distillation, solvent extraction, crystallisation, and the like.

For the compositions of the present invention comprising at least one monomethyltin compound, the monomethyltin trihalide may advantageously be prepared according to the process disclosed in EP-A-1 225 177.

The present invention also relates to the mono-alkyltin compounds, composition containing the same, as well as precursors thereof, as mentioned above, prepared starting from raw materials of renewable origin, i.e. starting from raw materials of nonfossil origin.

More precisely, by raw materials of renewable origin, one preferably understands the raw materials which include at least one carbon atom, preferably more than one, more preferably all carbon atoms, of renewable origin.

Compared to materials obtained from fossil raw materials, the compounds prepared from raw materials of renewable origin contain the isotope 14 of carbon ($^{14}C$). All carbon samples drawn from living organisms (animals or vegetables) are in fact a mixture of 3 isotopes: $^{12}C$ (accounting for approximately 98.892%), $^{13}C$ (approximately 1.108%) and $^{14}C$ (traces: approximately $1.2 \times 10^{-12}$%).

The $^{14}C/^{12}C$ ratio in living organisms is identical to that of the atmosphere. In the environment, $^{14}C$ exists in two dominating forms: mineral form, i.e. carbon dioxide ($CO_2$) and organic form, i.e. of carbon integrated in organic molecules.

In a living organism, the $^{14}C/^{12}C$ ratio is maintained constant by the metabolism because carbon is continuously exchanged with the environment. The proportion of $^{14}C$ being constant in the atmosphere, it is the same in the organism, as long as it is alive, since it absorbs $^{14}C$ as it absorbs $^{12}C$. The proportion of $^{14}C$ and $^{12}C$ did not change significantly during last thousands of years and the average ratio of $^{14}C/^{12}C$ is equal to approximately $1.2 \times 10^{-12}$.

The $^{12}C$ isotope is stable, i.e. the number of atoms of $^{12}C$ in a given sample is constant in the course of time. The $^{14}C$ isotope is radioactive (each gram of carbon from a living organism contains sufficient $^{14}C$ isotope to give 13.6 disintegrations per minute) and the content of $^{14}C$ in a sample decreases during a period of time (T) according to the following equation:

$$n = no^{(-at)}$$

wherein no is the original number of $^{14}C$ atoms (at the time of death of the animal or plant), n is the number of $^{14}C$ atoms remaining after the time period t, a is the desintegration constant (or radioactive constant), related to the half-life.

The half-life (or period), is the duration at the end of which an unspecified number of radioactive cores or unstable particles of a given species, is reduced by two-fold by disintegration; the half-life $T_{1/2}$ is related to the disintegration constant a according to the formula $aT_{1/2}$=ln 2. The half-life of $^{14}C$ is approximately 5730 years.

Given the half-life ($T_{1/2}$) of the $^{14}C$ isotope, one considers that the content of $^{14}C$ is constant since the extraction of the raw materials of renewable origin until the preparation of the compounds, compositions and precursors thereof, and even until the end of their uses.

According to the present invention, mono-alkyltin compounds, composition containing the same, as well as precursors thereof, can easily be obtained, in whole or in part, from raw materials of renewable origin. For example, the alkyl group of the alkyltin compounds may be prepared starting from alkenes, or corresponding alcohols, of biological origin (e.g. extraction from living organisms, plants, wood, animals, fish, or extraction from sugars, enzymatic preparation, bacterial fermentation, and the like).

Thus, mono-alkyltin compounds, composition containing the same, as well as precursors thereof according to the present invention, when they are prepared entirely or partly starting from raw materials of renewable origin, are characterized by the fact that they contain a quantity of isotope 14 of carbon higher than that of the same compounds, compositions or precursors thereof prepared exclusively starting from raw materials of fossil origin.

At present, there are at least two different techniques for measurement of the content of $^{14}C$ in a sample:

by spectrometry with liquid scintillation: this method consists in numbering the 'beta' (β) particles resulting from the disintegration of the $^{14}C$ isotope; the β-radiation resulting from a sample of known mass (a known number of atoms $^{12}C$) is measured during a certain time; this 'radioactivity' is proportional to the number of $^{14}C$ atoms, which can therefore be determined; the $^{14}C$ isotope present in the sample emits β-radiations, which, in contact with a scintillating liquid (scintillator), give rise to photons; these photons have different energies (between 0 keV and 156 keV) and form what is named a spectrum of $^{14}C$; according to alternatives of this method, the analysis is based either on the carbon dioxide produced beforehand by the carbonaceous sample in an appropriate absorbing solution, or on benzene after preliminary conversion of the carbonaceous sample into benzene;

by mass spectrometry: the sample is turned to graphite or to gaseous carbon dioxide, analyzed in a mass spectrometer; this technique uses an accelerator and a mass spectrometer to separate the $^{14}C$ ions from the $^{12}C$ ions and thus to determine the ratio of the two isotopes.

All these methods aiming at measuring the content of $^{14}C$ in the alkyltin compounds, compositions containing them and precursors thereof, are described in the ASTM D 6866 standard (in particular ASTM D 6866 06 of January 2006) and in ASTM D 7026 standard (in particular ASTM D 7026-04). The measurement method preferentially used in the field of the present invention is the mass spectrometry method described in ASTM D 6866 06 standard ("Radiocarbon and Isotope Ratio Mass Spectroscopy Analysis").

The alkyltin compounds, compositions containing them and precursors thereof prepared from at least one raw material of renewable origin are new and are therefore also part of the present invention. These compounds, compositions and precursors, are characterized by a $^{14}C$ content strictly greater than 0, more precisely a ratio $^{14}C/^{12}C$ strictly greater than 0 and lower or equal to approximately $1.2\times10^{-12}$, the value '0' indicating a compound which is exclusively obtained starting from carbon species of fossil origin, the value $1.2\times10^{-12}$ indicating a alkyltin compounds, compositions and precursors thereof prepared exclusively from carbon species of renewable origin.

The invention also relates to the use of the claimed composition mainly comprising monoalkyltin-based compounds as stabilisers for chlorine-containing polymers, glass coating chemicals and catalysts, and the like.

As stabiliser for chlorine-containing polymers, the composition of the present invention is of particular interest when the mono-alkyltin compound as major component is RSn(EHMA)$_3$, wherein R is chosen from among methyl, n-butyl, iso-octyl and n-octyl, preferably wherein R is n-octyl, and EHMA is 2-ethylhexyl-mercaptoacetate.

As catalyst, the composition of the present invention is of particular interest when the mono-alkyltin compound as major component is mono-alkyltin oxide/hydroxide, i.e. the reaction product of mono-alkyltin trihalide with T-H, wherein T is OH.

More specifically the claimed composition is useful as a stabiliser for chlorine-containing polymers. As chlorine-containing polymers, mention may be made of:

homopolymers and copolymers of vinyl chloride (PVC) and of vinylidene chloride (PVDC), vinyl resins comprising vinyl chloride units in their structure, such as copolymers of vinyl chloride, and vinyl esters of aliphatic acids, especially vinyl acetate, copolymers of vinyl chloride with esters of acrylic and methacrylic acid and with acrylonitrile, copolymers of vinyl chloride with diene compounds and unsaturated dicarboxylic acids or their anhydrides, such as copolymers of vinyl chloride with diethyl maleate, diethyl fumarate or maleic anhydride, post-chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and its copolymers with vinyl chloride and other polymerizable compounds;

polymers of vinyl chloroacetate and dichlorodivinyl ether; chlorinated polymers of vinyl carboxylate, such as vinyl acetate, vinyl propionate, vinyl butyrate, chlorinated polymeric esters of acrylic acid and of α-substituted acrylic acid, such as methacrylic acid, of nitriles, amides, alkyl esters such as acrylonitrile, (meth)acrylamide, methyl (meth)acrylate, butyl acrylate, ethyl acrylate, 2-ethylhexyl acrylate;

polymers of vinyl aromatic derivatives, such as styrene, dichlorostyrene; chlorinated rubbers;

chlorinated polymers of olefin, such as ethylene, propene, 1-butene, (2.2.1)bicyclo heptene-2, (2.2.1)bicyclo hepta-diene-2,5;

polymers and post-chlorinated polymers of chlorobutadiene and copolymers thereof with vinyl chloride, chlorinated natural and synthetic rubbers, and also mixtures of these polymers with one another or with other polymerizable compounds.

In the context of this invention, PVC also embraces copolymers with polymerizable compounds such as acrylonitrile, vinyl acetate or ABS, which can be suspension, bulk or emulsion polymers. Preference is given to PVC homopolymers and copolymers, optionally post-chlorinated, alone or in combination with polyacrylates.

Also included are graft polymers of PVC with EVA, ABS and MBS. Preferred substrates are also mixtures of the above-mentioned homo- and copolymers, especially vinyl chloride homopolymers, with other thermoplastic and/or elastomeric polymers, especially blends with homo- or copolymers as ABS (acrylonitrile-butadiene-styrene), MBS (methyl-methacrylate-butadiene-styrene), NBR (nitrile butadiene rubber), SAN (styrene-acrylonitrile), EVA (ethylene-vinyl acetate), CPE (chlorinated polyethylene), MBAS(methyl-methacrylate-butadiene-acrylonitrile-styrene), PMA (polyymethyl acrylate), PMMA (polymethylmethacrylate), EPDM (ethylene-propene-diene monomer) and polylactones.

These polymers (resins) can be thermoplastic and/or elastomeric. Examples of such components are compositions of (i) 20-80 parts by weight of a vinyl chloride homopolymer (PVC) and (ii) 80-20 parts by weight of at least one thermoplastic copolymer based on styrene and acrylonitrile, in particular from the group ABS, NBR, NAR, SAN and EVA. The abbreviations used for the copolymers are familiar to the person skilled in the art and have the following meanings: ABS: acrylonitrile-butadiene-styrene; SAN: styrene-acrylonitrile; NBR: acrylonitrile-butadiene; NAR: acrylonitrile-acrylate; EVA: ethylene-vinyl acetate.

Also suitable in particular are acrylate-based styrene-acrylonitrile copolymers (ASA). Preferred components in this context are polymer compositions comprising as components (i) and (ii) a mixture of 25-75% by weight PVC and 75-25% by weight of the abovementioned copolymers. Examples of such compositions are: 24-50% by weight PVC and 75-50% by weight copolymers of 40-75% by weight PVC and 60-25% by weight copolymers. Preferred copolymers are ABS, SAN and modified EVA, especially ABS, NBR, NAR and EVA are also particularly suitable.

It is possible for one or more of the abovementioned copolymers to be present. Particularly important components are compositions comprising (i) 100 parts by weight of PVC and (ii) 0-300 parts by weight of ABS and/or SAN-modified ABS and 0-80 parts by weight of the copolymers NBR, NAR and/or EVA, and especially EVA.

For stabilisation in the context of this invention, further suitable polymers are, in particular, recyclates of chlorine-containing polymers, these polymers being the polymers described in more detail above that have also undergone damage through processing, use or storage. PVC recyclate is particularly preferred. The recyclates may also include small amounts of extraneous substances, such as, for example, paper, pigments, adhesives, which are often difficult to remove. These extraneous substances may also arise from contact with various materials in the course of use or reprocessing, examples being residues of fuel, fractions of coating material, traces of metal and residues of initiator.

Preferably chlorine-containing polymers stabilised with the composition of the present invention are chosen from among polymers or mixtures of polymers chosen from among homopolymer vinyl halides such as polyvinyl chloride, polyvinylidene chloride, chlorinated polyvinyl chloride, post-chlorinated polyvinyl chloride and copolymers formed by the polymerisation of a vinyl halide monomer with up to 40% of a comonomer such as vinyl acetate, vinyl butyrate, vinylidene chloride, propylene, methylmethacrylate and the like.

The invention also includes chlorine-containing polymers containing other polymers such as chlorinated polyethylene; terpolymers of acrylonitrile, butadiene, styrene; terpolymers of methylmethacrylate, butadiene, styrene; polyacrylate resins; polymethylmethacylate resins and terpolymer of alkyl acrylate, methylmethacrylate, butadiene.

As hereinbefore described, known tin-based stabilisers are mixtures of mono- and di-alkyltin compounds, since it is known that monoalkyltin species provide a very good early colour to chlorine-containing polymers and dialkyltin species confer a good long term stability (colorhold) to these polymers.

It has now surprisingly been found that the composition of the present invention comprising a very high monoalkyltin compound content, ensures both early colour and colour retention, in chlorine-containing polymers.

The content of the claimed composition within the chlorine-containing polymers (resin) may vary in great proportions and is generally comprised between about 0.01 parts by weight and 10 parts by weight, preferably between about 0.1 and 7, more preferably from about 0.1 to about 5 and still more preferably between 0.4 and 2.5, parts by weight for 100 parts by weight of polymer(s).

One or more stabilising composition(s) of the present invention may be added to polymers or copolymers according to any procedure known in the art, and, by way of non limiting examples: as an emulsion or dispersion (e.g. in the form of a paste-like mixture), as a dry mix in the course of the mixing of additional stabilisers and/or polymer mixtures and/or additives, by direct addition to the processing apparatus (e.g. calendars, mixers, compounders, extruders and the like), or as a solution or melt or as flakes or pellets in dust-free form as a one-pack product.

Preferably, the composition(s) of the present invention is(are) added to the chlorine-containing polymer(s) according to the dry-blending method.

One or more stabilising composition(s) of the present invention may be added to the chlorine-containing polymers alone or as a formulation together with one or more other co-stabilisers known in the art, especially PVC co-stabilisers, and/or one or more additive(s). Alternatively, the composition of the present invention, co-stabiliser(s) and/or additives may be added concomitantly or sequentially into the above defined chlorine-containing polymer(s).

Co-stabilisers which may be present within said formulation, or more generally within the chlorine-containing polymer(s) together with the composition of the present invention may be for example chosen from among epoxydised soy bean oil, dihydropyridine compounds such as those described in FR 2 429 806, EP 0 027 439 or WO 2002/092686, and especially dihydropyridine and polydihydropyridine derivatives, more especially dihydro-1,4-dimethyl-2,6-dicarbododecyloxy-3,5-pyridine (Stavinor® D507, Arkema, referred to as "DHP" in the following description) or thiodiethanolbis-(5-methoxy-carbonyl-2,6-dimethyl-1,4-dihydropyridine-3-carboxylate (Synesal® M, Lagor), α-phenylindole, polyols, disaccharide alcohols, perchlorate compounds, glycidyl compounds, layered lattice compounds (hydrotalcite), zeolite compounds, phosphite compounds, β-diketones, β-ketoesters, mercaptocarboxylic esters, metal soaps, amino- and/or thiouracils, hydrazides, and the like and mixtures thereof.

Such co-stabilisers are well known to the skilled artisan and a detailed list of particularly advantageous co-stabilisers may be found in WO 2006/058789.

Examples of suitable polyols and disaccharide alcohols are pentaerythritol, dipentaerythritol, tripentaerythritol, trimethylolethane, bistrimethylolpropane, inositol (cyclitols), polyvinyl alcohol, bis-trimethylolethane, trimethylolpropane, sorbitol (hexitols), maltitol, isomaltitol, cellobiitol, lactitol, lycasine, mannitol, lactose, leucrose, tris(hydroxyethyl) isocyanurate, tris(hydroxypropyl) isocyanurate, palatinitol, tetramethylol-cyclohexanol, tetramethylolcyclopentanol, tetramethylolcyclopyranol, xylitol, arabinitol (pentitols), tetritols, glycerol, diglycerol, polyglycerol, thiodiglycerol or 1-O-α-D-glycopyranosyl-D-mannitol dihydrate. Of these, preference is given to the disaccharide alcohols.

Mention may also be made of polyol syrups, such as sorbitol, mannitol and maltitol syrup. The polyols and/or disaccharide compounds can be employed in an amount of, for example, from 0.01 to 20, judiciously from 0.1 to 20 and, in particular, from 0.1 to 10 parts by weight per 100 parts by weight of chlorine-containing polymers and resins, such as PVC.

Examples of perchlorate compounds are those of formula $M(ClO_4)_n$, in which M is Li, Na, K, Mg, Ca, Sr, Ba, Zn, Al, La or Ce. Depending on the valency of M, the index n is 1, 2 or 3. The perchlorate salts can be present as solutions or may be in the form of complexes with alcohols (polyols, cyclodextrins) or ether alcohols or ester alcohols. The ester alcohols also include the polyol partial esters. In the case of polyhydric alcohols or polyols, their dimers, trimers, oligomers and polymers are also suitable, such as di-, tri-, tetra- and polyglycols and also di-, tri- and tetrapentaerythritol or polyvinyl alcohol in various degrees of polymerisation.

Other suitable solvents are phosphate esters and also cyclic and acyclic carbonates. In this context, the perchlorate salts can be employed in various common forms of presentation; for example, as a salt or solution in water or an organic solvent as such, or adsorbed on a support material such as PVC, Ca silicate, zeolites or hydrotalcites, or bound by chemical reaction into a hydrotalcite or into another layered lattice compound. As polyol partial ethers, preference is given to glycerol monoethers and glycerol monothioethers. Further embodiments are described in EP 0 394 547, EP 0 457 471 and WO 94/24200.

Perchlorates can be employed in an amount of, for example, from 0.001 to 5, judiciously from 0.01 to 3, and, with particular preference, from 0.01 to 2 parts by weight per 100 parts by weight of chlorine-containing polymers and resins, such as PVC.

Glycidyl compounds that may be used as co-stabilisers are preferably those containing a glycidyl group directly bonded to carbon, oxygen, nitrogen or sulphur atoms. Examples are:

Glycidyl esters and β-methylglycidyl esters obtainable by reacting a compound having at least one carboxyl group in the molecule with epichlorohydrin or glyceroldichlorohydrin or β-methylepichlorohydrin, wherein the reaction advantageously takes place in the presence of bases.

As compounds having at least one carboxyl group in the molecule, mention may be made of aliphatic carboxylic acids, such as glutaric, adipic, pimelic, suberic, azelaic and sebacic acid or dimerised or trimerised linoleic acid, acrylic and methacrylic acid, caproic, caprylic, lauric, myristic, palmitic, stearic and pelargonic acid. Mention may also be made of cycloaliphatic carboxylic acids, such as, for example, cyclohexanecarboxylic, tetrahydrophthalic, 4-methyltetrahydrophthalic, hexahydrophthalic and 4-methylhexahydrophthalic acids. Aromatic carboxylic acids can also be used, examples being benzoic, phthalic, isophthalic, trimellitic and pyromellitic acid. It is likewise possible to make use of carboxyl-terminated adducts of, for example, trimellitic acid with polyols, such as glycerol or 2,2-bis(4-hydroxycyclohexyl)propane. Other epoxide compounds which can be used in the context of this invention are given in EP 0 506 617.

Glycidyl ethers or β-methylglycidyl ethers obtainable by reacting a compound having at least one free alcoholic hydroxyl group and/or phenolic hydroxyl group with an appropriately substituted epichlorohydrin under alkaline conditions or in the presence of an acidic catalyst with subsequent alkali treatment.

Ethers of this type are derived, for example, from acyclic alcohols, such as ethylene glycol, diethylene glycol and higher poly(oxyethylene) glycols, propane-1,2-diol, or poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, bis(tri-methylol)propane, pentaerythritol, sorbitol, and from polyepichlorohydrins, butanol, amyl alcohol, pentanol, and from monofunctional alcohols such as isooctanol, 2-ethylhexanol, isodecanol and also $C_7$-$C_9$-alkanol and $C_9$-$C_{11}$-alkanol mixtures. They are also derived, however, for example, from cycloaliphatic alcohols, such as 1,3- or 1,4-dihydroxycyclohexane, bis(4-hydroxycyclohexyl)methane, 2,2-bis-(4-hydroxycyclohexyl)propane or 1,1-bis(hydroxymethyl)cyclohex-3-ene, or they possess aromatic nuclei, such as N,N-bis(2-hydroxyethyl)aniline or p,p'-bis(2-hydroxyethylamino)diphenylmethane. The epoxide compounds can also be derived from mononuclear phenols, such as, for example, from phenol, resorcinol or hydroquinone; or, they are based on polynuclear phenols, such as, for example, on bis(4-hydroxyphenyl)methane, 2,2-bis(4-hydroxyphenyl)propane, 2,2-bis(3,5-dibromo-4-hydroxyphenyl)-propane, on 4,4'-dihydroxydiphenyl sulphone or on condensates of phenols with formaldehyde obtained under acidic conditions, such as phenol novolacks. Examples of further possible terminal epoxides are: glycidyl-1-naphthyl ether, glycidyl 2-phenylphenyl ether, 2-biphenylyl glycidyl ether, N-(2,3-epoxypropyl)phthalimide and 2,3-epoxypropyl 4-methoxyphenyl ether.

N-Glycidyl compounds obtainable by dehydrochlorination of the reaction products of epichlorohydrin with amines containing at least one amino hydrogen atom. These amines are, for example, aniline, N-methylaniline, toluidine, n-butylamine, bis(4-aminophenyl)methane, m-xylylenediamine or bis(4-methylaminophenyl)methane, and also N,N,O-triglycidyl-m-aminophenol or N,N,O-triglycidyl-p-aminophenol. However, the N-glycidyl compounds also include N,N'-di, N,N',N"-tri- and N,N',N",N"'-tetraglycidyl derivatives of cycloalkyleneureas, such as ethyleneurea or 1,3-propyleneurea and N,N'-diglycidyl derivatives of hydantoins, such as of 5,5-dimethylhydantoin or glycoluril and triglycidyl isocyanurate.

S-Glycidyl compounds such as di-S-glycidyl derivatives derived from dithiols, such as ethane-1,2-dithiol or bis(4-mercaptomethylphenyl)ether, for example.

Epoxy compounds are for example, (3'-4'-epoxy-6'-methylcyclohexyl)methyl-3,4-epoxy-6-methylcyclohexanecarboxylate. Examples of suitable terminal epoxides are: a) liquid bisphenol A diglycidyl ethers, such as Araldit® GY 240, Araldit® GY 250, Araldit® GY 260, Araldit® GY 266, Araldit® GY 2600, Araldit® MY 790; b) solid bisphenol A diglycidyl ethers, such as Araldit® GT 6071, Araldit® GT 7071, Araldit® GT 7072, Araldit® GT 6063, Araldit® GT 7203, Araldit® GT 6064, Araldit® GT 7304, Araldit® GT 7004, Araldit® GT 6084, Araldit® GT 1999, Araldit® GT 7077, Araldit® GT 6097, Araldit® GT 7097, Araldit® GT 7008, Araldit® GT 6099, Araldit® GT 6608, Araldit® GT 6609, Araldit® GT 6610; c) liquid bisphenol F diglycidyl ethers, such as Araldit® GY 281, Araldit® PY 302, Araldit® PY 306; d) solid polyglycidyl ethers of tetraphenylethane, such as CG Epoxy Resin 0163; e) solid and liquid polyglycidyl ethers of phenol-formaldehyde novolack, such as EPN 1 138, EPN 1 139, GY 1180, PY 307; f) solid and liquid polyglycidyl ethers of o-cresol-formaldehyde novolack, such as ECN 1235, ECN 1273, ECN 1280, ECN 1299; g) liquid glycidyl ethers of alcohols, such as Shell Glycidyl ether 162, Araldit® DY 0390, Araldit® DY 0391; h) liquid glycidyl ethers of carboxylic acids, such as Shell Cardura® E terephthalic acid ester, trimellitic acid ester, Araldit® PY 284; i) solid heterocyclic epoxy resins (triglycidyl isocyanurate), such as Araldit® PT 810; j) liquid cycloaliphatic epoxy resins such as Araldit® CY 179; k) liquid N,N,O-triglycidyl ethers of p-aminophenol, such as Araldit® MY 0510; l) tetraglycidyl-4,4'-methylenebenzamine or N,N,N',N'-tetraglycidyl-diamino-phenylmethane, such as Araldit® MY 720, and Araldit® MY 721. Preference is given to the use of epoxy compounds having two functional groups. In principle, however, it is also possible to employ epoxy compounds having one, three or more functional groups. Use is made predominantly of epoxy compounds, especially diglycidyl compounds, having aromatic groups.

If desired, it is also possible to employ a mixture of different epoxy compounds. Particular preference is given as terminal epoxy compounds to diglycidyl ethers based on bisphenols, such as on 2,2-bis(4-hydroxyphenyl)propane (bisphenol A), bis(4-hydroxyphenyl)methane or mixtures of bis(ortho/para-hydroxyphenyl)methane (bisphenol F), for example.

The terminal epoxy compounds can be employed in an amount of preferably at least 0.1 part, for example from 0.1 to 50, judiciously from 1 to 30 and in particular, from 1 to 25 parts by weight, per 100 parts by weight of chlorine-containing polymers and resins, such as PVC.

Examples of hydrotalcites that may be used as co-stabilisers are compounds known to the person skilled in the art, for example, from DE 384 35 81, EP 0 062 813 and WO 1993/20135.

Compounds from the series of the hydrotalcites can be described by the following general formula:

$$M^{2+}_{1-x}M^{3+}_{x}(OH)_2(An^{b-})_{x/b}\cdot dH_2O$$

wherein
$M^{2+}$ represents one or more metals from the group Mg, Ca, Sr, Zn and Sn, $M^{3+}$ represents Al or B,
An is an anion having the valency n,
b is a number from 1-2,
$0<x<0.5$
m is a number from 0-20 and
d is a number in the range from 0 to 300, preferably in the range from 0.5 to 30. Preferably An is $OH^-$, $ClO_4^-$, $HCO_3^-$, $CH_3COO^-$, $C_6H_5COO^-$, $CO_3^{2-}$, $(CHOHCOO)_2^{2-}$, $(CH_2COO)_2^{2-}$, $CH_3CHOHCOO^-$, $HPO_3^-$ or $HPO_4^{2-}$.

Examples of hydrotalcites are $Al_2O_3 6MgO\ CO_2\ 12H_2O$ (i), $Mg_{4.5}\ Al_2\ (OH)_{13}CO_2\ 3.5H_2O$ (ii), $4MgO\ Al_2O_3\ CO_2\ 9H_2O$ (iii), $4MgO\ Al_2O_3\ CO_2\ 6H_2O$, $ZnO\ 3MgO\ Al_2O_3\ CO_2\ 8-9H_2O$ and $ZnO\ 3MgO\ Al_2O_3\ CO_2\ 5-6H_2O$. Very particular preference is given to types i, ii and iii.

Zeolite co-stabilisers may be all kinds of zeolites known in the art, such as those described by the following general formula:

$$M_{x/n}[(AlO_2)x(SiO_2)_y]\cdot wH_2O$$

in which n is the charge of the cation M;
M is an element from the first or second main group, such as Li, Na, K, Mg, Ca, Sr or Ba;
y:x is a number from 0.8 to 15, preferably from 0.8 to 1.2;
and w is a number from 0 to 300, preferably from 0.5 to 30. Examples of zeolites are sodium aluminosilicates of the following types: zeolite A, sodalite, zeolite Y, zeolite X, zeolite LSX; or the zeolites preparable by complete or partial replacement of the Na atoms by Li, K, Mg, Ca, Sr or Zn atoms.

Preferred zeolites are zeolite A, sodalite; zeolite Y, zeolite X; and those X zeolites having an Si/Al ratio of about 1:1 called LSX for Low Silica X, or the zeolites preparable by complete or partial replacement of the Na atoms by Li, K, Mg, Ca, Sr, Ba or Zn atoms. The zeolites indicated can also be lower in water content, or anhydrous.

Further suitable zeolites are zeolite P, zeolite MAP or the zeolites preparable by complete or partial replacement of the Na atoms by Li, K and/or H atoms, such as zeolite K—F, zeolite D, as described for instance in Barrer et al., J. Chem. Soc., (1952), 1561-71, and in U.S. Pat. No. 2,950,952; also suitable are the following zeolites: K offretite, zeolite R, zeolite LZ-217, Ca-free zeolite LZ-218, zeolite T, zeolite LZ-220, zeolite L, zeolite LZ-211, zeolite LZ-212, zeolite 0, zeolite LZ-217, zeolite LZ-219, zeolite Rho, zeolite LZ-214, zeolite ZK-19, zeolite W (K-M), zeolite ZK-5, zeolite Q. Particular preference is given to zeolite P grades of the above formula in which x is from 2 to 5 and y is from 3.5 to 10, and very particular preference is given to zeolite MAP of the standard formula in which x is 2 and y is from 3.5 to 10. In particular, the zeolite concerned is zeolite Na—P, i.e. M is Na. This zeolite generally occurs in the variants Na—P-1, Na—P-2 and Na—P-3, which differ in their cubic, tetragonal or orthorhombic structure (see R. M. Barrer, B. M. Munday, J. Chem. Soc. A, (1971), 2909-14). The above literature reference also describes the preparation of zeolite P-1 and P-2. According to that reference, Zeolite P-3 is very rare and is therefore of virtually no practical interest. The structure of the zeolite P-1 corresponds to the gismondite structure known from the abovementioned "Atlas of Zeolite Structures". In EP-A-0 384 070, a distinction is made between cubic (zeolite B or Pc) and tetragonal (zeolite P1) zeolites of the P type. Also mentioned therein are zeolites of the P type having Si:Al ratios below 1.07:1. These are zeolites having the designation MAP or MA-P, for "Maximum Aluminium P".

Depending on the preparation process, zeolite P may also include small fractions of other zeolites. Highly pure zeolite P has been described in WO 1994/26662. Within the scope of the invention, it is also possible to use those finely divided, water-insoluble sodium aluminosilicates which have been precipitated and crystallised in the presence of water-soluble organic or inorganic dispersants. These can be introduced into the reaction mixture in any desired manner, prior to or during the precipitation and crystallization.

Very particular preference is given to Na zeolite A and Na zeolite P. The hydrotalcites and/or zeolites can be employed in amounts, for example, from 0.1 to 20, judiciously from 0.1 to 10 and, in particular, from 0.1 to 5 parts by weight per 100 parts by weight of chlorine-containing polymers and resins, such as PVC.

As examples of phosphites (phosphorous triesters), thiophosphites and thiophosphates, mention may be made of triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol diphosphite, bis(2,4-di-tert-butyl-6-methylphenyl) pentaerythritol diphosphite, bis(2,4,6-tri-tertbutylphenyl) pentaerythritol diphosphite, tristearyl sorbitol triphosphite, bis(2,4-di-tert-butyl-6-methylphenyhl) methylphenyl)methyl phosphite, bis(2,4-di-tert-butyl-6-methylphenyl)ethyl phosphite.

Particularly suitable are trioctyl, tridecyl, tridodecyl, tritetradecyl, tristearyl, trioleyl, triphenyl, tricresyl, tris-p-nonylphenyl or tricylcohexyl phosphite and, with particular preference, the aryl dialkyl and alkyl diaryl phosphites, examples being phenyl didecyl, 2,4-di-tert-butylphenyl didodecyl phosphite, 2,6-di-tert-butylphenyl didodecyl phosphite and the dialkyl and diaryl pentaerythritol diphosphites, such as distearyl pentaerythritol diphosphite, and also non-stoichiometric triaryl phosphites whose composition is, for example, $(H_{19}C_9-C_6H4)O_{1-5}P(OC_{12,13}H_{25,27})_{1.5}$ or $(H_8C_{17}-C_6H_4)O_2P(i-C_8H_{17}O)$ or $(H_{19}C_9-C_6H_4)O_{1.5}P(OC_{9,11}H_{19,23})_{1.5}$.

Preferred organic phosphites are distearyl pentaerythritol diphosphite, trisnonylphenyl phosphite and phenyl didecyl phosphite. Other suitable phosphites are phosphorous diesters (with abovementioned radicals) and phosphorous monoesters (with abovementioned radicals), possibly in the form of their alkali metal, alkaline earth metal, zinc or aluminium salts. It is also possible for these phosphorous esters to have been applied to an alumo salt compound; in this regard see also DE-A-403 18 18.

The organic phosphites can be employed in an amount of, for example, from 0.01 to 10, judiciously from 0.05 to 5 and, in particular, from 0.1 to 3 parts by weight per 100 parts by weight of chlorine-containing polymers and resins, such as PVC.

By thiophosphites and thiophosphates are meant compounds of the general type $(RS_3P, (RS_3P=O$ and $(RS)_3P=S$, respectively, as are described, for instance, in patents DE 2 809 492, EP 0 090 770 and EP 0 573 394. Examples of these compounds are trithiohexyl phosphite, trithio-octyl phosphite, trithiolauryl phosphite, trithiobenzyl phosphite, trithiophosphorous acid tris(carbo-iso-octyloxy)methyl ester, trithiophosphorous acid tris(carbotrimethylcyclohexyloxy) methyl ester, trithiophosphoric acid S,S,S-tris(carbo-iso-octyloxy)methyl ester, trithiophosphoric acid S,S,S-tris(carbo-2-ethylhexyloxy)methyl ester, trithiophosphoric acid S,S,S-tris-1-(carbohexyloxy)ethyl ester, trithiophosphoric acid S,S,S-tris-1-(carbo-2-ethylhexyloxy)ethyl ester and trithiophosphoric acid S,S,S-tris-2-(carbo-2-ethylhexyloxy) ethyl ester.

Among the β-diketones and β-keto esters that may be used, mention may be made of 1,3-dicarbonyl compounds, which can be linear or cyclic dicarbonyl compounds. Preference is given to the use of dicarbonyl compounds of the following formulae: $R'_1COCHR'_2—COR'_3$ in which $R'_1$, is $C_1$-$C_{22}$-alkyl, $C_5$-$C_{10}$-hydroxyalkyl, $C_2$-$C_{18}$-alkenyl, phenyl, OH—, $C_1$-$C_4$-alkyl-, $C_1$-$C_4$-alkoxy- or halogen-substituted phenyl, $C_7$-$C_{10}$-phenylalkyl, $C_5$-$C_{12}$-cycloalkyl, $C_1$-$C_4$-alkyl-substituted $C_5$-$C_{12}$-cycloalkyl or a group —$R'_5$—S—$R'_6$ or —$R'_5$—O—$R'_6$, $R'_2$ is hydrogen, $C_1$-$C_8$-alkyl, $C_2$-$C_{12}$-alkenyl, phenyl, $C_7$-$C_{12}$-alkylphenyl, $C_7$-$C_{10}$-phenylalkyl or a group —CO—$R'_4$, $R'_3$ is as defined for $R'_1$ or is $C_1$-$C_{18}$-alkoxy, $R'_4$ is $C_1$-$C_4$-alkyl or phenyl, $R'_5$ is $C_1$-$C_{10}$-alkylene and $R'_6$ is $C_1$-$C_{12}$-alkyl, phenyl, $C_7$-$C_{18}$-alkylphenyl or $C_7$-$C_{10}$-phenylalkyl.

These include the hydroxyl-containing diketones of EP 0 346 279 and the oxa and thia diketones of EP 0 307 358, as well as the keto esters based on isocyanic acid of U.S. Pat. No. 4,339,383.

$R'_1$ and $R'_3$ as alkyl can in particular be $C_1$-$C_{18}$-alkyl, such as, for example methyl, ethyl, n-propyl, isopropyl, n-butyl, tert-butyl, pentyl, hexyl, heptyl, octyl, decyl, dodecyl or octadecyl. $R'_1$ and $R'_3$ as hydroxyalkyl are in particular a group —$(CH_2)_n$—OH, in which n is 5, 6 or 7.

$R'_1$ and $R'_3$ as alkenyl can for example be vinyl, allyl, methallyl, 1-butenyl, 1-hexenyl or oleyl, preferably allyl. $R'_1$, and $R'_3$ as OH—, alkyl-, alkoxy- or halogen-substituted phenyl can for example be tolyl, xylyl, tert-butylphenyl, methoxyphenyl, ethoxyphenyl, hydroxyphenyl, chlorophenyl or dichlorophenyl. $R'_1$ and $R'_3$ as phenylalkyl are in particular benzyl. $R'_2$ and $R'_3$ as cycloalkyl or alkylcycloalkyl are, in particular, cyclohexyl or methylcyclohexyl. $R'_2$ as alkyl can in particular be $C_1$-$C_4$-alkyl. $R'_2$ as $C_2$-$C_{12}$-alkenyl can in particular be allyl. $R'_2$ as alkylphenyl can in particular be tolyl. $R'_2$ as phenylalkyl can in particular be benzyl.

Preferably, $R'_2$ is hydrogen. $R'_3$ as alkoxy can for example be methoxy, ethoxy, butoxy, hexyloxy, octyloxy, dodecyloxy, tridecyloxy, tetradecyloxy or octadecyloxy. $R'_5$ as $C_1$-$C_{10}$-alkylene is, in particular, $C_2$-$C_4$-alkylene. $R'_6$ as alkyl is, in particular, $C_4$-$C_{12}$-alkyl, such as, for example butyl, hexyl, octyl, decyl or dodecyl. $R'_6$ as alkylphenyl is in particular tolyl. $R'_6$ as phenylalkyl is in particular benzyl.

Examples of 1,3-dicarbonyl compounds of the above formula and their alkali metal, alkaline earth metal and zinc chelates are acetylacetone, butanoylacetone, heptanoylacetone, sterolyacetone, palmitoylacetone, lauroylacetone, 7-tert-nonylthio-2,4-heptanedione, benzoylacetone, dibenzoylmethane, lauroylbenzoylmethane, palmitoylbenzoylmethane, stearoylbenzoylmethane, isooctylbenzoylmethane, 5-hydroxycapronyl-benzoylmethane, tribenzoylmethane, bis (4-methylbenzoyl)methane, benzoyl-p-chlorobenzoyl-methane, bis(2-hydroxybenzoyl)methane, 4-methoxybenzoyl-benzoylmethane, bis(4-methoxybenzoyl)methane, 1-benzoyl-1-acetylnonane, benzoylacetylphenylmethane, stearoyl-4-methoxybenzoylmethane, bis(4-tert-butyl-benzoyl)methane, benzoylformylmethane, benzoylphenylacetylmethane, biscyclohexanoylmethane, di-pivaloylmethane, 2-acetylcyclopentanone, 2-benzoylcyclopentanone, methyl, ethyl and allyl diacetoacetate, methyl and ethyl benzoyl-, propionyl- and butyrylacetoacetate, triacetylmethane, methyl, ethyl, hexyl, octyl, dodecyl or octadecyl acetoacetate, methyl, ethyl, butyl, 2-ethylhexyl, dodecyl or octadecyl benzoylacetate, and also $C_1$-$C_{18}$-alkyl propionylacetates and butyrylacetates; ethyl, propyl, butyl, hexyl or octyl stearoylacetate, and also polycyclic .beta.-keto esters, as described in EP 0 433 230, and dehydraacetic acid, and the zinc, magnesium or alkali metal salts thereof.

Preference is given to 1,3-diketo compounds of the above formula in which $R'_1$ is $C_1$-$C_{18}$-alkyl, phenyl, OH—, methyl- or methoxy-substituted phenyl, $C_7$-$C_{10}$-phenylalkyl or cyclohexyl, $R'_2$ is hydrogen and $R'_3$ is as defined for $R'_1$. The 1,3-diketo compounds can be employed in amount of, for example, from 0.01 to 10, judiciously from 0.01 to 3 and, in particular, from 0.01 to 2 parts by weight per 100 parts by weight of chlorine-containing polymers and resins, such as PVC C (post-chlorinated polyvinyl chloride).

Examples of mercaptocarboxylic esters includes esters of thioglycolic acid, thiomalic acid, mercaptopropionic acid, mercaptobenzoic acids and thiolactic acid, mercaptoethyl stearate and mercaptoethyl oleate, as are described in FR 2 459 816, EP 0 090 748, FR 2 552 440 and EP 0 365 483. The generic mercaptocarboxylic esters also embrace polyol esters and partial esters thereof, and also thioethers derived from them. These molecules may also be latent-mercaptides as described in EP 0 945 485.

Metal soaps for use as co-stabilisers in the present invention include, as examples, primarily metal carboxylates of preferably relatively long-chain carboxylic acids. Familiar examples are stearates and laurates, and also oleates and salts of shorter-chain alkanecarboxylic acids. Alkylbenzoic acids are also said to be included under metal soaps.

Metals that may be mentioned are Li, Na, K, Mg, Ca, Sr, Ba, Zn, Al, La, Ce and rare earth metals. Use is often made of what are known as synergistic mixtures, such as barium/zinc, magnesium/zinc, calcium/zinc or calcium/magnesium/zinc stabilisers. The metal soaps can be employed individually or in mixtures. A review of common metal soaps is given in Ullmann's Encyclopedia of Industrial Chemistry, $5^{th}$, Ed., Vol. A16 (1985), p. 361 sqq.). It is judicious to use organic metal soaps from the series of the aliphatic saturated $C_2$-$C_{22}$ carboxylates, the aliphatic unsaturated $C_3$-$C_{22}$ carboxylates, the aliphatic $C_2$-$C_{22}$ carboxylates substituted by at least one OH group, the cyclic and bicyclic carboxylates having 5-22 carbon atoms, the unsubstituted benzenecarboxylates substituted by at least one OH group and/or by $C_1$-$C_{16}$-alkyl, the unsubstituted naphthalenecarboxylates substituted by at least one OH group and/or by $C_1$-$C_{16}$-alkyl, the phenyl-$C_1$-$C_{16}$-alkylcarboxylates, the naphthyl-$C_1$-$C_{16}$-alkylcarboxylates or the unsubstituted or $C_1$-$C_{12}$-alkyl-substituted phenolates, tallates and resinates.

Named examples which may be mentioned are the zinc, calcium, magnesium or barium salts of monovalent carboxylic acids such as acetic, propionic, butyric, valeric, hexanoic, enanthoic, octanoic, neodecanoic, 2-ethylhexanoic, pelargonic, decanoic, undecanoic, dodecanoic, tridecanoic, myristic, palmitic, isostearic, stearic, 12-hydroxystearic, behenic, benzoic, p-tert-butylbenzoic, 3,5-di-tert-butyl-4-hydroxybenzoic, toluic, dimethylbenzoic, ethylbenzoic, n-propylbenzoic, salicylic, p-tert-octylsalicyclic and sorbic acid; calcium, magnesium and zinc salts of the monoesters of divalent carboxylic acids such as oxalic, malonic, succinic, glutaric, adipic, fumaric, pentane-1,5-dicarboxylic, hexane-1,6-dicarboxylic, heptane-1,7-dicarboxylic, octane-1,8-dicarboxylic, phthalic, isophthalic, terephthalic and hydroxyphthalic acid; and of the di- or triesters of tri- or tetra-valent carboxylic acids such as hemimellitic, trimellitic, pyromellitic and citric acid.

Preference is given to calcium, magnesium and zinc carboxylates of carboxylic acids having 7 to 18 carbon atoms (metal soaps in the narrow sense), such as, for example, benzoates or alkanoates, preferably stearate, oleate, laurate, palmitate, behenate, hydroxystearates, dihydroxystearates or 2-ethylhexanoate. Particular preference is given to stearate, oleate and p-tert-butylbenzoate. Overbased carboxylates, such as overbased zinc octoate, are also preferred. Preference is likewise given to overbased calcium soaps. If desired, it is also possible to employ a mixture of carboxylates of different structures. Preference is given to compositions, as described, comprising an organozoic and/or organocalcium compound.

Other named examples of metal soaps or metal salts which may be mentioned are dimetallic salts of dicarboxylic acids such as dilithium, disodium or dipotassium salts of divalent carboxylic acids such as of oxalic, malonic, succinic, glutaric, adipic, fumaric, pentane-1,5-dicarboxylic, hexane-1,6-dicarboxylic, heptane-1,7-dicarboxylic, octane-1,8-dicarboxylic, phthalic, isophthalic and terephthalic. Preference is given to disodium adipate.

In addition to the compounds mentioned, organoaluminum compounds are also suitable, as are compounds analogous to those mentioned above, especially aluminium tristearate, aluminium distearate and aluminium monostearate, and also aluminium acetate and basic derivatives derived therefrom. Further information on the aluminium compounds, which can be used and are preferred is given in U.S. Pat. No. 4,060,512 and U.S. Pat. No. 3,243,394.

Also suitable in addition to the compounds already mentioned are organic rare earth compounds, especially compounds analogous to those mentioned above. The term rare earth compound means especially compounds of the elements cerium, praseodymium, neodymium, samarium, europium, gadolinium, terbium, dysprosium, holmium, erbium, thulium, ytterbium, lutetium, lanthanum and yttrium; mixtures, especially with cerium, being preferred. Further preferred rare earth compounds can be found in EP 0 108 023.

It is possible if desired to employ a mixture of zinc, alkali metal, alkaline earth metal, aluminium, cerium, lanthanum or lanthanoid compounds of different structure. It is also possible for organozinc, organoaluminum, organocerium, organo-alkali metal, organo-alkaline earth metal, organolanthanum or organolanthanoid compounds to be coated on an alumo salt compound; in this regard see also DE 403 18 18.

The metal soaps and/or mixtures thereof can be employed in an amount of, for example, from 0.001 to 10 parts by weight, judiciously from 0.01 to 8 parts and, with particular preference, from 0.05 to 5 parts by weight per 100 parts by weight of chlorine-containing polymers and resins, such as PVC. The same applies to the further metal stabilisers.

As regards further metal stabilisers, mention may be made of the organometallic stabilisers and in particular of the organotin stabilisers. These can be the carboxylates, maleates, mercaptides and sulphides, in particular. Examples of suitable compounds are described in U.S. Pat. No. 4,743,640, U.S. Pat. No. 2,567,651, U.S. Pat. No. 2,598,936, U.S. Pat. No. 2,567,652, U.S. Pat. No. 6,174,941, U.S. Pat. No. 5,925,696, U.S. Pat. No. 6,156,830, U.S. Pat. No. 6,084,013, U.S. Pat. No. 6,194,494, U.S. Pat. No. 4,105,627, U.S. Pat. No. 4,352,903, DE 2,427,853.

Further customary additives can also optionally be added in addition to the composition of the present invention in chlorine-containing polymers. As these additives, mention may be made of stabilisers, auxiliaries and processing aids, examples being alkali metal compounds and alkaline earth metal compounds, lubricants, plasticisers, pigments, fillers, epoxidized fatty acid esters, antioxidants, UV absorbers and light stabilisers, optical brighteners, impact modifiers and processing aids, gelling agents, antistats, biocides, metal passivators, flame retardants, blowing agents, anti-fog agents, compatibilizers and anti plate-out agents, and the like, as well as mixtures thereof. Such additives are commonly known in the art, and disclosed, for example in "Handbook of PVC Formulating" by E. J. Wickson, John Wiley & Sons, New York, (1993).

Examples of such additives are as follows:

Fillers and reinforcing agents are, for example, calcium carbonate, dolomite, wollastonite, magnesium oxide, magnesium hydroxide, silicates, china clay, talc, glass fibres, glass beads, wood flour, mica, metal oxides, or metal hydroxides, carbon black, graphite, rock flour, heavy spar, glass fibres, talc, kaolin and chalk. The fillers can be employed in an amount of for example, from 5 to 80, judiciously from 10 to 40 and, in particular, from 10 to 20 parts by weight per 100 parts by weight of chlorine-containing polymers and resins, such as PVC.

Alkali metal and alkaline earth metal compounds. By these are meant principally the carboxylates of the above-described metal soaps, but also corresponding oxides and/or hydroxides or carbonates. Also suitable are mixtures thereof with organic acids. Examples are LiOH, NaOH, KOH, CaO, $Ca(OH)_2$, MgO, $Mg(OH)_2$, $Sr(OH)_2$, $Al(OH)_3$, $CaCO_3$ (also basic carbonates, such as magnesia alba and hutite), and also Na and K salts of fatty acids. In the case of alkaline earth metal and Zn carboxylates it is also possible to employ their adducts with MO or M(OH)$_2$ (M=Ca, Mg, Sr or Zn), known as "overbased" compounds. In addition to the stabiliser combination of the invention it is preferred to employ alkali metal carboxylates, alkaline earth metal carboxylates and/or aluminium carboxylates.

Lubricants, examples of which are montan wax, fatty acid esters, PE waxes, amide waxes, chlorinated paraffins, glycerol esters or alkaline earth metal soaps. Lubricants which can be used are also described in "Kunststoffadditive", R. Gachter; H. Muller, Carl Hanser Verlag, 3rd Ed., (1989), pages 478-488. Mention may also be made of fatty ketones (as described in DE 42 04 887) and of silicone-based lubricants (as described in EP 0 225 261) or combinations thereof, as set out in EP 0 259 783. Calcium stearate is preferred. The lubricants can also be applied to an alumo salt compound; in this regard see also DE 403 18 18.

Plasticisers, and examples of suitable organic plasticisers are those from the following groups: A) Phthalates: examples of such plasticisers are dimethyl, diethyl, dibutyl, dihexyl, di-2-ethylhexyl, di-n-octyl, di-iso-octyl, di-iso-nonyl, di-iso-decyl, di-iso-tridecyl, dicyclohexyl, dimethylcyclohexyl, dimethylglycol, dibutylglycol, benzyl butyl and diphenyl phthalates, and also mixtures of phthalates, such as $C_7$-$C_9$— and $C_9$-$C_{11}$-alkyl phthalates obtained from predominantly linear alcohols, $C_6$-$C_{10}$-n-alkyl phthalates and $C_8$-$C_{10}$-n-alkyl phthalates. Of these preference is given to dibutyl, dihexyl, di-2-ethylhexyl, di-n-octyl, di-iso-octyl, di-iso-nonyl, di-iso-decyl, di-iso-tridecyl and benzyl butyl phthalate, and the stated mixtures of alkyl phthalates. Particular preference is given to di-2-ethylhexyl,di-isononyl and di-iso-decyl phthalate, which are also known by the common abbreviations DOP (dioctyl phthalate, di-2-ethylhexyl phthalate), DINP (di-iso-nonyl phthalate) and DIDP (diisodecyl phthalate); B) Esters of aliphatic dicarboxylic acids, especially esters of adipic, azelaic and sebacic acid: examples of such plasticisers are di-2-ethylhexyl adipate, diisooctyl adipate (mixture), di-iso-nonyl adipate (mixture), diisodecyl adipate (mixture), benzyl butyl adipate, benzyl octyl adipate, di-2-ethylhexyl azelate, di-2-ethylhexyl sebaceate and diisodecyl sebaceate (mixture), di-2-ethylhexyl adipate and di-iso-octyl adipate being preferred; C) Trimellitates, examples being tri-2-ethylhexyl trimellitate, tri-iso-decyl trimellitate (mixture), tri-iso-tridecyl trimellitate, tri-iso-octyl trimellitate (mixture) and also tri-$C_6$-$C_8$-alkyl, tri-$C_6$-$C_{10}$-alkyl, tri-$C_7$-$C_9$-alkyl- and tri-$C_9$-$C_{11}$-alkyl trimellitates. The latter trimellitates are formed by esterification of trimellitic acid with the corresponding alkanol mixtures. Preferred trimellitates are tri-2-ethylhexyl trimellitate and the abovementioned trimellitates from alkanol mixtures. Customary abbreviations are TOTM (trioctyl trimellitate, tri-2-ethylhexyl trimellitate), TIDTM (tri-iso-decyl trimellitate) and TITDTM (tri-iso-tridecyl trimellitate); D) Epoxy plasticisers: these are primarily epoxidized unsaturated fatty acids, such as epoxidized soybean oil; E) Polymer plasticisers: a definition of these plasticisers and examples of them are given in "Kunststoffadditive", R. Gachter; H. Muller, Carl Hanser Verlag, 3rd ed., (1989), section 5.9.6, pages 412-415, and also in "PVC Technology", W. V. Titow, 4th ed., Elsevier Publ., (1984), pages 165-170. The most common starting materials for preparing the polyester plasticisers are dicarboxylic acids, such as adipic, phthalic, azelaic and sebacic acids; diols, such as 1,2-propanediol, 1,3-butanediol, 1,4-butanediol, 1,6-hexanediol, neo-pentyl glycol and diethylene glycol; F) Phosphoric esters: a definition of these esters is given in the abovementioned "Taschenbuch der Kunststoffadditive" section 5.9.5, pp. 408-412. Examples of such phosphoric esters are tributyl phosphate, tri-2-ethylbutyl phosphate, tri-2-ethylhexyl phosphate, trichloroethyl phosphate, 2-ethylhexyl diphenyl phosphate, cresyl diphenyl phosphate; triphenyl phosphate, tricresyl phosphate and trixylenyl phosphate. Preference is given to tri-2-ethylhexyl phosphate and to Reofos(R) 50 and 95 (Ciba Spezialitatenchemie); G) Chlorinated hydrocarbons (paraffins); H) Hydrocarbons; I) Monoesters, e.g., butyl oleate, phenoxyethyl oleate, tetrahydrofurfuryl oleate and alkylsulphonic esters; J) Glycol esters, e.g., diglycol benzoates. Definitions and examples of plasticizers of groups G) to J) are given in the following handbooks: "Kunststoffadditive", R. Gachter/H. Muller, Carl Hanser Verlag, 3rd ed., 1989, section 5.9.14.2, pp. 422-425, (group G), and section 5.9.14.1, p. 422, (group H). <11> PVC Technology", W. V. Titow, 4th ed., Elsevier Publishers, 1984, section 6.10.2, pages 171-173, (group G), section 6.10.5 page 174, (group H), section 6.10.3, page 173, (group I) and section 6.10.4, pages 173-174 (group J). It is also possible to use mixtures of different plasticizers. The plasticizers can be employed in an amount of, for example, from 5 to 20 parts by weight, judiciously from 10 to 20 parts by weight, per 100 parts by weight of chlorine-containing polymers and resins, such as PVC. Rigid or semi rigid PVC contains preferably up to 10%, with particular preference up to 5% of plasticiser, or no plasticiser.

As other additives, pigments may be used, suitable substrates of which are known to the person skilled in the art. Examples of inorganic pigments are $TiO_2$, zirconium oxide-based pigments, $BaSO_4$, zinc oxide (zinc white) and lithopones (zinc sulphide/barium sulphate), carbon black, carbon black/titanium dioxide mixtures, iron oxide pigments, $Sb_2O_3$, (Ti, Ba, Sb)$O_2$, $Cr_2O_3$, spinels, such as cobalt blue and cobalt green, Cd(S, Se), ultramarine blue. Organic pigments are, for example, apigments, phthalocyanine pigments, quinacridone pigments, perylene pigments, diketopyrrolopyrrole pigments and anthraquinone pigments. Preference is also given to $TiO_2$ in micronised form.

Epoxidized fatty acid esters and other epoxy compounds may also be used as additives to the chlorine-containing polymers together with the stabilising composition of the invention. Particularly suitable such esters are those of fatty acids from natural sources (fatty acid glycerides), such as soybean oil or rapeseed oil. It is, however, also possible to employ synthetic products such as epoxidized butyl oleate. Epoxidized polybutadiene and polyisoprene can also be used, as they are or in partially hydroxylated form, or else homo- or copolymeric glycidyl acrylate and glycidyl methacrylate can be used. These epoxy compounds can also have been applied to an alumo salt compound; in this regard see also DE 031 818.

Customary antioxidants may also be used as additives, alone or in combination. Examples of suitable antioxidants are alkylated monophenols, for example, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, 2,6-dinonyl- 4-methylphenol, 2,4-dimethyl-6-(1'-methylundec-1'-yl)phenol, 2,4-dimethyl-6-(1'-methylheptadex-1'-yl)phenol, 2,4-dimethyl-6-(1'-methyltridec-1'-yl)phenol, octylphenol, nonylphenol, dodecylphenol and mixtures thereof.

Other examples are alkylthiomethylphenols, such as 2,4-dioctylthiomethyl-6-tert-butylphenol, 2,4-dioctylthiomethyl-6-methylphenol, 2,4-dioctylthiomethyl-6-ethylphenol, and 2,6-didodecylthiomethyl-4-nonylphenol; alkylated hydroquinones, such as 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxy-anisole, 3,5-di-tert-butyl-4-hydroxyanisole, 3,5-di-tert-butyl-4-hydroxyphenyl stearate, bis(3,5-di-tert-butyl-4-hydroxyphenyl) adipate; hydroxylated thiodiphenyl ethers, such as 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol)-4,4'-bis-(2,6-dimethyl-4-hydroxyphenyl)disulphide; alkylidenebisphenols, such as 2,2'-methylenebis(6-tert-butyl-4-methylphenol), 2,2'-methylenebis(6-tert-butyl-4-ethylphenol), 2,2'-methylene bis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis-(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylene bis(2,6-di-tert-butylphenol), 4,4'-methylene bis-(6-tert-butyl-2-methylphenol), 1,1-bis-(5-tert-butyl-4-hydroxy-2-methylphenyl)butane, 2,6-bis-(3-tert-butyl-5-methyl-2-hydroxybenzyl)-4-methylphenol, 1,1,3-tris-(5-tert-butyl-4-hydroxy-2-methyl-phenyl)butane, 1,1-bis-(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methyl-phenyl)dicyclo-pentadiene, bis[2-(3'-tert-butyl-2'-hydroxy-5'-methylbenzyl)-6-tert-butyl-4-methyl-phenyl]terephthalate, 1,1-bis-(3,5-dimethyl-2-hydroxyphenyl)butane, 2,2-bis-(3,5-di-tert-butyl-4-hydroxyphenyl)propane, 2,2-bis(4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane; benzyl compounds, such as 3,5,3',5'-tetra-tert-butyl-4,4'-dihydroxy-dibenzyl ether, octadecyl 4-hydroxy-3,5-dimethyl benzyl-mercaptoacetate, tris(3,5-di-tert-butyl-4-hydroxybenzyl)amine, bis(4-tert-butyl-3-hydroxy-2,6-dimethyl benzyl)-dithioterephthalate, bis (3,5-di-tert-butyl-4-hydroxybenzyl) sulphide, isooctyl 3,5-di-tert-butyl-4-hydroxybenzyl-mercaptoacetate; hydroxybenzylated malonates, for example, di-octadecyl 2,2-bis(3,5-di-tert-butyl-2-hydroxybenzyl)malonate, di-oactadecyl 2-(3-tert-butyl-4-hydroxy-5-methylbenzyl)malonate, di-dodecyl mercapto-ethyl-2,2-bis(3,5-di-tert-butyl-4-hydroxybenzyl)malonate, di-[4-(1,1,3,3-tetramethylbutyl)-phenyl]-2,2-bis(3,5-di-tert-butyl-4-hydroxybenzyl) malonate; aromatic hydroxybenzyl compounds, for example, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol; triazine compounds, such as 2,4-bisoctylmercapto-6-(3,5-di-tert-butyl-4-hydroxyanilino)-1,3,5-triazine, 2-octylmercapto-4,6-bis-(3,5-di-tert-butyl-4-hydroxyanilino)-1,3,5-triazine, 2-octylmercapto-4,6-bis-(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris-(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris-(3,5-dicyclohexyl-4-hydroxybenzyl) isocyanurate; phosphates and phosphonites, for example, dimethyl-2,5-di-tert-butyl-4-hydroxybenzylphosphonate, diethyl-3,5-di-tert-butyl-4-hydro-oxybenzylphosphonate, dioctadecyl-3,5-di-tert-butyl-4-hydroxybenzylphosphonate, dioctadecyl-5-tert-butyl-4-hydroxy-3-methylbenzylphosphonate, calcium salt of monoethyl 3,5-di-tert-butyl-4-hydroxybenzylphosphonate, tetrakis-(2,4-di-tert-butylphenyl)-4,4'-biphenylenediphosphonite, 6-isooctyloxy-2,4,8,10-tetra-tert-butyl-12H-dibenzo-[d,g]-1,3,2-dioxaphosphocine, 6-fluoro-2,4,8,10-tetra-tert-butyl-1 2-methyl-dibenzo-[d,g]-1,3,2-dioxaphosphocine; acylaminophenols, such as 4-hydroxylauranilide, 4-hydroxystearanilide, octyl N-(3,5-di-tert-butyl-4-hydroxyphenyl)carbamate; esters of β-(3,5-di-tert-butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propane diol, neo-pentyl glycol, thiodiethylene glycol, diethylene glycol, triethylene glycol, pentaerythritol, dipentaerythritol, tris(hydroxyethyl) isocyanurate, N,N'-bis (hydroxyethyl)oxalamide, 3-thia-undecanol, 3-thia-pentadecanol, trimethylhexanediol, trimethylolpropane, ditrimethylolpropane, 4-hydroxymethyl-1-phospha-2,6,7-trioxabicyclo[2.2.2]octane; esters of β(5-tert-butyl-4-hydroxy-3-methylphenyl)propionic acid with mono- or polyhydric alcohols, for example, with methanol, ethanol, octanol, octadecanol, 1,6-hexanediol, 1,9-nonanediol, ethylene glycol, 1,2-propanediol neo-pentyl glycol, thiodiethylene glycol, diethylene glycol, triethylene glycol, pentaerythritol, tris(hydroxy)ethyl isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane; esters of β-(3,5-dicyclohexyl-4-hydroxyphenyl)propionic acid with mono- or polyhydric alcohols, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pantaerythritol, tris(hydroxy)ethyl isocyanurate, N,N'-bis(hydroxyethyl)oxalamide, 3-thia-undecanol, 3-thiapentadecanol, trimethylhexanediol, trimethylolpropane, 4-hydroxymethyl-1-phospha-2,6,7-trioxabicyclo[2.2.2]octane; esters of 3,5-di-tert-butyl-4-hydroxyphenylacetic acid with mono- or polyhydric alcohols, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalamide, 3-thia-undecanol, 3-thiapentadecanol, trimethylhexanediol, trimethylpropane, 4-hydroxymethyl-1-phospha-2,6,7-trioxabicyclo[2.2.2]octane; amides of β-(3,5-di-tert-butyl-4-hydroxyphenyl)propionic acid, such as, for example, N,N'-bis(3,5-di-tert-butyl-4-hydroxyphenylpropionyl) hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine; vitamin E (tocopherol) and derivatives.

As antioxidants, preference is given to 2,2-bis(4-hydroxyphenyl)propane, esters of 3,5-di-tert-butyl-4-hydroxyphenylpropionic acid with octanol, octadecanol or pentaerythritol or tris(2,4-di-tert-butylphenyl) phosphite. It is also possible, if desired, to employ a mixture of antioxidants of different structures.

The antioxidants can be employed in an amount of, for example, from 0.01 to 10 parts by weight judiciously from 0.1 to 10 parts by weight and in particular, from 0.1 to 5 parts by weight per 100 parts by weight of PVC.

Other additives may be UV absorbers and light stabilisers, examples of which are 2-(2'-hydroxyphenyl)benzotriazoles, such as, for example 2-(2'-hydroxy-5'-methylphenyl)benzotriazole, 2-(3',5'-di-tert-butyl-2'-hydroxyphenyl)benzotriazole, 2-(5'-tert-butyl-2-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzothiazole, 2-(3',5'-bis(α,α-dimethylbenzyl)-2'-hydroxyphenyl)benzothiazole, mixtures of 2-(3'-tert-butyl-2'-hydroxy-5'-(2-octyloxycarbonylethyl)phenyl, O-chlorobenzotriazole, 2-(3'-tert-butyl-5'-[2-(2-ethylhexyloxy)carbonylethyl]-2'-hydroxyphenyl)-5-chlorobenzotri-azole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl] benzotriazole with polyethylene glycol 300; where R=3'-tert-butyl-4'-hydroxy-5'-2H-benzotriazol-2-yl-phenyl; 2-hydroxybenzophenones, for example the 4-hydroxy-, 4-methoxy-, 4-octyloxy-, 4-decyloxy, 4-dodecyloxy-, 4-benzyloxy, 4,2',4'-trihydroxy-, 2'-4,4'-dimethoxy-derivatives; esters of substituted or unsubstituted benzoic acids, for example 4-tert-butylphenyl salicylate, phenyl salicylate, octylphenyl salicylate, dibenzoylresorcinol, bis(4-tert-butyl-benzoyl)resorcinol, benzoylresorcinol, 2,4-di-tert-butylphenyl 3,5-di-tert-butyl-4-hydroxybenzoate, hexadecyl-3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate; acrylates, for example ethyl-α-cyano-β,β-diphenylacrylate or isooctyl-ethyl-α-cyano-β,β-diphenylacrylate, methyl-α-carbo-methoxycinnamate, methyl-α-cyano-β-methyl-para-methoxycinnamate or butyl-α-cyano-β-methyl-para-methoxycinnamate, methyl-α-carbomethoxy-para-methoxycinnamate, N-(β-carbomethoxy-cyanovinyl)-2-methylindoline; nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters such as the methyl or ethyl ester, of 4-hydroxy-3,5-di-tert-butylbenzylphosphonic acid, nickel complexes of ketoximes, such as of 2-hydroxy-4-methylphenylundecylketoxime, nickel complexes of 1-phenyl-4-lauroyl-5-hydroxypyrazole, with or without additional ligands; oxalamides, for example 4, 4'-dioctyloxyoxanilide, 2,2'-dioctyloxy-5,5'-di-tert-butyl-oxanilide, 2,2'-didodecyloxy-5,5'-di-tert-butyloxanilide, 2-ethoxy-2'-ethyl-oxanilide, N,N'-bis(3-dimethylaminopropyl)oxalamide, 2-ethoxy-5-tert-butyl-2'-ethyloxyanilide and its mixture with 2-ethoxy-2'-ethyl-5,4'-di-tert-butyl-oxanilide, mixtures of ortho- and para-methoxy and of ortho- and para-ethoxy-di-substituted oxanilides; 2-(2-hydroxyphenyl)-1,3,5-triazines, for example 2, 4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethyl-phenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1, 3,5-triazine; sterically hindered amines, for example bis(2,2, 6,6-tetramethyl-piperidin-4-yl) sebaceate, bis(2,2,6,6-tetramethylpiperidin-4-yl)succinate, bis(1,2,2,6,6-pentamethylpiperidin-4-yl)sebaceate, bis(1-octyloxy-2,2,6, 6-tetramethylpiperidin-4-yl)sebaceate, bis(1,2,2,6,6-pentamethylpiperidyl) n-butyl-3,5-di-tert-butyl-4-hydroxybenzylmalonate; the condensate of 1-hydroxyethyl-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2, 6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis (3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl), 2-n-butyl-2(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebaceate, bis(1-octyloxy-2,2,6,6-tetramethyl-piperidyl)succinate, linear or cyclic condensates of N,N'-bis(2,2,6,6-tetramethyl-4-piperidyl)hexamethylenediamine and 4-morpholino-2,6-dichloro-1,3,5-triazine; the condensate of 2-chloro-4,6-di-(4-n-butylamino-2,2,6,6-tetramethylpiperidyl)-1,3,5-triazine and 1,2-bis(3-aminopropylamino) ethane, the condensate of 2-chloro-4,6-di(4-n-butylamino-1, 2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidone-2, 5-dione, 3-dodecyl-1-(1,2,2,6,6-pentamethyl-4-piperidyl) pyrrolidine-2,5-dione, mixtures of 4-hexadecyloxy- and 4-stearyloxy-2,2,6,6-tetramethylpiperidine; the condensate of N,N'-bis(2,2,6,6-tetramethyl-4-piperidyl)hexamethylendiamine and A-cyclohexylamino-2,6-dichloro-1,3,5-triazine, the condensate of 1,2-bis(3-aminopropylamino)ethane and 2,4,6-trichloro-1,3,5-triazine, and also 4-butylamino-2,2,6,6-tetramethylpiperidine (CAS Reg. No. [136504-96-6]); N-(2, 2,6,6-tetramethyl-4-piperidyl)-n-dodecylsuccinimide, N-(1, 2,2,6,6-pentamethyl-4-piperidyl)-n-dodecylsuccinimide, 2-undecyl-7,7,9,9-tetramethyl-1-oxa-3,8-diaza-4-oxo-spiro [4.5]decane; 1,1-bis(1,2,2,6,6-pentamethyl-4-piperidyloxy-carbonyl)-2-(4-methoxyphenyl)ethene, N,N'-bisformyl-N, N'-bis(2,2,6,6-tetramethyl-4-piperidyl) hexamethylenediamine, the diester of A-methoxymethylenemalonic acid with 1,2,2,6,6-pentamethyl-4-hydroxypiperidine, poly[methylpropyl-3-oxy-4-(2, 2,6,6-tetramethyl-4-piperidyl)]siloxane; the reaction product of maleic anhydride-α-olefin copolymer and 2,2,6,6-tetramethyl-4-aminopiperidine or 1,2,2,6,6-pentamethyl-4-aminopiperidine.

Still as additives, mention may be made of blowing agents, examples thereof being organic aand hydracompounds, tetrazoles, oxazines, isatoic anhydride, and also sodium carbonate and sodium bicarbonate. Preference is given to azodicarboxamide and sodium bicarbonate and mixtures thereof.

Still other additives may be used in the context of the present invention, and among them, mention may be made of impact modifiers, thermal modifiers, processing aids, gelling agents, antistatic agents, biocides, fungicides, metal passivators, optical brighteners, flame retardants, antifogging agents and compatibilizers, which are described in "Kunststoffadditive", R. Gachter; H. Muller, Carl Hanser Verlag, 3rd ed., 1989, and in the "Handbook of Polyvinyl Chloride Formulating" E. J. Wickson, J. Wiley & Sons, 1993, and in "Plastics Additives" G. Pritchard, Chapman & Hall, London, 1st ed., 1998. Impact modifiers are also described in detail in "Impact Modifiers for PVC", J. T. Lutz/D. L. Dunkelberger, John Wiley & Sons, 1992.

The compositions of the present invention can also contain other stabilisers such as amino-uracils and particularly 6-aminouracils disclosed for instance in U.S. Pat. No. 6,174,941 B1 and/or thiouracils and particularly 4-amino-6-hydroxy-2-mercapto-pyrimidine.

Hydrazides and hydrazide systems may also be used as additives. Preferred hydrazides are selected among one or more hydrazides compounds of formula $R^{11}$—CO—NH—$R^{12}$, in which $R^{11}$ is chosen from among:
$C_1$-$C_{30}$ linear or branched alkyl and $C_2$-$C_{30}$ mono- or poly-unsaturated hydrocarbon, each of these groups possibly containing one or more heteroatoms, and possibly being substituted with one or more phenyl groups (substituted or not), epoxy groups, cycloaliphatic or heterocyclic group, halogen atom(s), hydroxy and/or alkoxy, phenyl, benzyl, naphthyl, toluoyl group, optionally substituted by —OH, —Cl, -alkoxy, -alkyl, -cycloalkyl, —COOR" or OCOR" (where R" is $C_1$-$C_{12}$ alkyl), thienyl, —CH=CH—CO—NH—NH—$R^{21}$, —X—CO—NH—NH$_2$, —CH=CH—CO—$R^{14}$, —(CH$_2$)$_n$—C$_6$H$_5$ (with n varying from 1 to 5), —NH—NH$_2$;

$R^{12}$ is chosen from hydrogen and the group —CO—$R^{13}$;

$R^{13}$ and $R^{14}$, which may be the same or different are chosen from among $C_1$-$C_{30}$ linear or branched alkyl and $C_2$-$C_{30}$ mono- or poly-unsaturated hydrocarbon, each of these groups possibly containing one or more heteroatoms, and possibly being substituted with one or more phenyl groups (substituted or not), epoxy groups, cycloaliphatic or heterocyclic group, halogen atom(s), hydroxy and/or alkoxy; phenyl, benzyl, naphthyl, toluoyl group, optionally substituted by —OH, —Cl, -alkoxy, -alkyl, -cycloalkyl, —COOR" or OCOR" (where R" is $C_1$-$C_{12}$ alkyl);

X is chosen from among $C_1$-$C_{30}$ linear or branched alkylene and $C_2$-$C_{30}$ mono- or poly-unsaturated bivalent hydrocarbon, each of these groups possibly containing one or more heteroatoms, and possibly being substituted with one or more phenyl groups (substituted or not), epoxy groups, cycloaliphatic or heterocyclic group, halogen atom(s), hydroxy and/or alkoxy, phenylene, benzylene, naphthylene, toluoylene group, optionally substituted by —OH, —Cl, -alkoxy, -alkyl, -cycloalkyl, —COOR" or OCOR" (where R" is $C_1$-$C_{12}$ alkyl);

$R^{11}$ and $R^{12}$ also possibly be linked by a covalent bond when $R^{11}$=—CH=CH— and $R^{12}$=—CO— (ketonic function).

Preferred hydrazides are those for which at least one hydrazide is such as $R^{11}$ is $C^1$-$C^{17}$ alkyl group (e.g. methyl, butyl, octyl, ethyl-2-hexyl, stearyl, lauryl); —X—CO—NHNH$_2$ where X is $C_1$-$C_{17}$ alkyl (e.g. methyl, butyl, octyl, ethyl-2-hexyl, stearyl, lauryl), or 1,3-phenyl group substituted or not; ortho-substituted phenol, benzenic cycle, isophthalic group, naphthol, cyclo-S-pentadiene-2,4, $C_6H_5$—$CH_2$— and $R^{12}$ is H, COR$^{13}$ with R$^{13}$ being preferably chosen from among $C_1$-$C_{17}$ alkyl (e.g. methyl, butyl, octyl, ethyle-2-hexyle, stearyl, lauryl) and a benzenic ring).

Particularly preferred co-stabilisers and additives are chosen from among epoxydised soy bean oil, hydrotalcite, zeolite, dihydropyridine-based compounds as described hereinbefore, α-phenylindole, β-diketones, phosphates, polyols, THEIC (isocyanurate), metallic salts (especially Zn, Mg, or Ca stearate(s)), acetylacetonate (acac) salts such as Ca(acac)$_2$, perchlorate-based compounds (such as sodium or potassium perchlorates), and the like, as well as mixtures thereof.

According to another embodiment of the present invention, preferred co-stabilisers are chosen from among dihydropyridine compounds. Particularly valuable compositions of the invention comprise dihydro-1,4-dimethyl-2,6-dicarbododecyloxy-3,5-pyridine (Stavinor® D507, Arkema, or "DHP") as co-stabiliser. Particularly advantageous mixtures of co-stabiliser and additive may be for example mixtures of DHP with sodium perchlorate.

Therefore, according to another aspect, the present invention relates to a formulation comprising at least one composition of the invention as disclosed above, i.e. a composition mainly comprising at least one monoalkyltin-based compound as a major compound, and at least one dihydropyridine-based compound, preferably dihydro-1,4-dimethyl-2,6-dicarbododecyloxy-3,5-pyridine, and optionally at least one perchlorate compound, preferably sodium perchlorate.

Still according to another embodiment of the present invention, preferred co-stabilisers are chosen from among metal soaps or metals salts of carboxylic acids. Particularly valuable compositions of the invention comprise disodium diadipate as co-stabiliser.

Still other conventional additives may be added to the composition according to the invention, and to the optional co-stabiliser(s). This additive may be all and any additives used in the domain of application and the nature of which will be evident for the skilled artisan.

The present invention also relates to chlorine-containing polymers comprising at least one composition as defined above, and optionally at least one co-stabiliser, such as defined above, preferably a dihydropyridine-based compound, such as DHP, and/or one or more additive(s), such as previously described, preferably a perchlorate compound, such as sodium perchlorate.

Because of the high content of mono-alkyltin species, and the low content of the di-alkyltin species, and the very low (traces) of tri-alkyltin species within the compositions of the present invention, said compositions present a low to very low toxicity versus di- and/or tri-alkyltin compound compositions. More particularly the compositions of the present invention are less toxic than (and even non toxic according to the regulations when compared to) the known and used compositions containing both mono- and di-alkyltin species, wherein the weight ratio of mono- to di-alkyltin species is less than 90/10.

According to another embodiment, the composition of the present invention may be used to stabilise chlorine-containing polymers as defined above (matrix), said chlorine-containing polymers being processed by any method known in the art, such as, for example, extrusion, calendaring, injection, injection-moulding, to prepare articles based on the said matrix.

According to a preferred embodiment, the amount of composition within the chlorine-containing polymers ranges from 0.2 to 5 phr and preferably 0.5 to 3 phr (the term "phr" means per hundred of resin). Still according to another preferred embodiment, the thermal stability may even be increased by adding a friction or shear rate controlling agent, a viscosity controlling agent, or mixtures thereof, and particularly a viscosity reducing agent and/or a friction or shear rate decreasing agent. Friction or shear rate controlling, and particularly reducing, agents are well known in the art, as are the viscosity controlling, and particularly reducing agents. Friction or shear rate can also be decreased by processing conditions, according to known techniques of the art. Similarly viscosity can also be reduced by modifying the structure of the halogenated resin, for example when the chlorine-containing polymers is a copolymer, again according to techniques well known in the art.

The stabilised polymers in accordance with the invention can be prepared in a manner known per se using devices known per se such as the abovementioned processing apparatus to mix the stabilising composition of the invention and any further additives with the polymers. In this case, the stabilisers can be added individually or as a mixture or else in the form of so-called master batches.

The stabilised polymers in accordance with the present invention can be brought into the desired form by known methods. Examples of such methods are milling, calendering, extruding, injection moulding or spinning, and also extrusion blow moulding. The stabilised polymers can also be processed to foam materials.

Stabilised polymers in accordance with the invention are suitable, for example, for the manufacture of hollow articles (bottles), packaging films (thermoform sheets), blown films, pipes, foam materials, heavy profiles (window frames), transparent-wall profiles, construction profiles, sidings, fittings, office films, and apparatus enclosures (computers, domestic appliances). Preference is given to rigid or semi-rigid PVC films (opaque or transparent), PVC rigid foam articles and PVC pipes for drinking water or wastewater, pressure pipes, gas pipes, cable-duct and cable protection pipes, pipes for industrial pipelines, seepage pipes, flow-off pipes, guttering pipes and drainage pipes. For further details on this subject see "Kunststoffhandbuch PVC", Vol. 2/2, W. Becker/H. Braun, $2^{nd}$ ed., (1985), Carl Hanser Verlag, pages 1236-1277.

The present invention also relates to articles comprising at least one polymer matrix and at least one composition according to the present invention, and optionally one or more additive(s) and/or co-stabiliser(s), as hereinbefore described.

According to a preferred embodiment of the invention, the article is a rigid or semi-rigid, opaque or transparent film, especially those chosen from among rigid or semi-rigid, opaque or transparent films, shrink-films, adhesive films, sheets, fittings, profiles (window, in-door), edge-bands.

Preferably, the article is an opaque or transparent rigid or semi-rigid film, which may be advantageously used for thermoforming (or not) and preparing food-packaging, pharmaceutical blisters, plastic cards (such as credit cards), furniture films and technical packaging films, and generally all kinds of opaque and transparent films.

The present invention is now illustrated with the following examples, which do not aim at limiting the sought scope of protection, which is defined by the annexed claims.

EXAMPLES

Part 1

Preparation of Monoalkyltin Compounds

Example 1

Distillation of Mono-Octyltin Trichloride from a Thermal Redistribution Mixture of Octyltin Chlorides A mixture (928 g) consisting of mono-octyltin trichloride (59.0%), di-octyltin dichloride (39.5%), tin tetrachloride (1.2%) and tri-octyltin chloride (0.3%) that resulted from a thermal redistribution of tetra-octyltin and $SnCl_4$ (1:2 molar ratio), was fractionally distilled at 8 mbar. The distillate (520 g) collected at a vapour temperature of 145° C., consisted of mono-octyltin trichloride (99.3%), di-octyltin dichloride (0.5%) and tin tetrachloride (0.2%) according to GC analysis after ethylation with excess EtMgCl.

Example 2

Mono-Octyltin Tris((2-Ethylhexyl)Mercaptoacetate)

2-Ethylhexylmercaptoacetate (371 g; 1.82 mol) and water (102 g) were added under stirring to 200 g (0.589 mol) of mono-octyltin trichloride obtained from Example 1. Then 290 g (1.81 mol) of a 25% solution of sodium hydroxide (NaOH) in water was added in ca. 1.5 hours at a reaction temperature of 50° C.

After the reaction the pH of the water layer was adjusted to pH=5-6 and the two phases were allowed to separate. The water layer was drained and volatiles were removed by distillation (10 mbar) up to a pot temperature of 110° C. The product was filtered through 8 µm filter paper using Dicacel as filter aid to afford 462 g (93%) of the final product.

GC analysis after ethylation with excess EtMgCl indicated that the purity of this product was >99.5% with less than 0.5% di-octyltin bis(2-ethylhexylmercaptoacetate) being present. Tri-organotin species were not detectable (<0.1%).

Example 3

Re-Distillation of Mono-Octyltin Trichloride Obtained from Thermal Redistribution Re-distillation of mono-octyltin trichloride (at 8 mbar, 145° C.) that had been obtained from the procedure described in Example 1, afforded mono-octyltin trichloride in 99.7% purity (by GC analysis after ethylation with excess EtMgCl) with only a small quantity of di-octyltin dichloride (0.03%).

Example 4

Mono-Octyltin Tris((2-Ethylhexylmercaptoacetate)

2-Ethylhexylmercaptoacetate (744 g; 3.64 mol) and 204 g of water were added under stirring to 400 g (1.18 mol) of mono-octyltin trichloride from Example 3. Then 567 gram (3.54 mol) of a 25% solution of NaOH in water was added in ca. 2 hours at a reaction temperature of 50° C.

After the reaction the pH of the water layer was adjusted to pH=5-6 and the two phases were allowed to separate. The water layer was drained and volatiles were removed by distillation (10 mbar) up to a pot temperature of 110° C. The product was filtered through 8 μm filter paper using Dicacel as filter aid to afford 985 gram (98%) of the final product.

GC analysis after ethylation with excess EtMgCl, indicated that the purity of this product was 97.9% with minor amounts of other species being present: tin tetrakis(2-ethyl hexyl mercaptoacetate) (0.26%), di-octyltin bis(2-ethylhexylmercaptoacetate) (<0,1%), tri-octyltin (2-ethylhexylmercaptoacetate) (<0,01%).

Example 5

Mono-Octyltin Trichloride from 1-Octene, HCl and $SnCl_2$,

A reaction vessel equipped with magnetic stirring, was brought under inert atmosphere and charged with 0.55 g of $Pd(PPh_3)_4$ (0.46 mmol). Next, 110 mL of a 0.80 M solution of anhydrous $SnCl_2$ in THF (88 mmol) were added, followed by 220 mL of 1-octene (1.40 mol). The vessel was placed in an oil bath and heated to 50° C. Subsequently, 332 mL of a 0.25 M HCl solution in THF (83 mmol) were added and the resulting pale yellow solution was stirred for 1.5 hours at 50° C.

Volatiles were removed in vacuum (80° C., 70 mbar) and hexane (100 mL) was added to the resulting suspension. Filtration followed by concentration in vacuum afforded 24.5 g of a yellow-orange liquid that, according to GC-analysis (after alkylation with excess EtMgCl), consisted of mono-octyltin trichloride (89.7%), di-octyltin dichloride (0.09%), tri-octyltin chloride (<0,01%) and residual solvent.

Example 6

Mono-Octyltin Tris((2-Ethylhexylmercaptoacetate)

2-ethylhexylmercaptoacetate (37.0 g; 0.181 mol) and 8.90 g of water were added under stirring to 20.64 g (0.058 mol) of mono-octyltin trichloride obtained from Example 5. Then 26.5 g (0.17 mol) of a 25% solution of NaOH in water was added in ca. 2 hours at a reaction temperature of 50° C.

After the reaction the pH of the water layer was adjusted to pH=5-6 and the two phases were allowed to separate. The water layer was drained and volatiles were removed by distillation (9 mbar) up to a pot temperature of 110° C. The product was filtered through 8 μm filter paper using Dicacel as filter aid to afford 41.6 g of the final product.

GC analysis after ethylation with excess EtMgCl, indicated that this product consisted of mono-octyltin tris((2-ethylhexylmercaptoacetate) (95.4%) and di-octyltin bis(2-ethylhexylmercaptoacetate) (<0,1%). Residual solvent as measured by measuring the weight loss on drying at 50° C. (3.0%) and residual 2-ethylhexylmercaptoacetate (not quantified) accounted for the remaining weight of the sample. A sample of this compound was tested for PVC stabilisation.

Part 2

Application Examples

In the following examples, the term "phr" means per hundred of poly(vinyl chloride) (PVC) resin (e.g.: 0.2 phr means 0.2 g per 100 g of PVC). All parts are given by weight.

Example A

Comparative Study of Monoalkyltin—Vs. Dialkyltin Compounds on Long Term Colorhold Retention in PVC Transparent Rigid Films A PVC formulation typical for transparent rigid film (amounts of each component in phr are given below) is evaluated using a Collin two-roll mill, the rolls of which are heated to 200° C. The rotational speeds of the two cylinders are respectively adjusted to 20 rpm and 24 rpm, providing sufficient friction to gelate PVC and sufficient heat to thoroughly study the thermal stabilisation efficiency of stabilisers. The gap between the cylinders is adjusted to 0.5 mm. Samples are withdrawn from the cylinders at regular time intervals, their coloration being recorded.

The components of the various PVC formulations and their amounts are the following:

| | |
|---|---|
| PVC (Lacovyl RB8010, Arkema, kW = 57): | 100 |
| Epoxydised soybean oil (Ecepox PB3, Arkema) | 1 |
| Hydrogenated castor oil (Loxiol G15, Henkel) | 0.6 |
| Oxidized PE wax (A-C 316A, Honeywell) | 0.12 |
| Process aid (Plastistrength 551, Arkema) | 0.6 |
| Antisticking process aid (Plastistrength 770, Arkema) | 1 |
| MBS impact modifier (Clearstrength 320, Arkema) | 8 |
| Stabiliser (cf. list below) | 1.3 |

The various stabilisers are the following:
Stab 1=Composition of Example 6 comprising high purity mono-octyltin-(2-ethylhexylmercaptoacetate);
Stab 2=30% mono octyl tin (2-ethylhexylmercaptoacetate) and 70% di-octyltin-(2-ethylhexylmercaptoacetate);
Stab 3=60% mono octyl tin (2-ethylhexylmercaptoacetate) and 40% di-octyltin-(2-ethylhexylmercaptoacetate).

The b* value in Hunter L*a*b* scale (b*, ASTM Standard E 313) is measured on each sample withdrawn and the results are reported in Table 1 below:

TABLE 1

| t (min.) | Stab 1 (according to the invention) | Stab 2 (comparative) |
|---|---|---|
| 2 | 7.1 | 7 |
| 3 | 7.8 | 7.8 |
| 4 | 8.4 | 9.2 |
| 5 | 9.4 | 10.5 |
| 6 | 9.9 | 13.3 |
| 7 | 10.1 | 14.6 |
| 8 | 12.1 | 16.9 |
| 9 | 13.0 | 18.0 |
| 10 | 15.7 | 21.1 |
| 12 | 22.2 | 26.5 |
| 15 | 43.6 | 53.7 |

The results listed in Table 1 above show the efficiency of the stabiliser containing a high content of mono-alkyltin compound, i.e. high purity mono-alkyltin compound as described in the present invention, not only on the initial colour of the PVC formulation but also on the long term colorhold retention compared to formulations containing both mono- and di-alkyltin compounds.

Example B

Comparative Study of Mono-Alkyltin Vs. Di-Alkyltin Compounds on Long Term Colorhold Retention in PVC Used in Film Calendaring Production A PVC formulation containing a copolymer widely used in film calendering production (amounts of each component in phr are given below) is evaluated using a Collin two-roll mill, the rolls of which are brought to 190° C. The rotational speeds of the two to cylinders are respectively adjusted to 20 rpm and 24 rpm, providing sufficient friction to gelate PVC and sufficient heat to thoroughly study the thermal stabilisation efficiency of stabilisers. The gap between the cylinders is adjusted to 0.5 mm. Samples are withdrawn from the cylinders at regular time intervals, their coloration being recorded.

The components of the PVC formulation and their amounts are the following:

| | |
|---|---|
| PVC (Lacovyl SO71, Arkema, kW = 57): | 60 |
| Copolymer vinyl chloride - vinyl acetate (Lacovyl GA 7701H, Arkema KW = 57) | 40 |
| Epoxydised soybean oil (Ecepox PB3, Arkema) | 1 |
| Glycerol mono-oleate (Loxiol G10, Henkel) | 0.7 |
| Pentaerythritol adipate stearate (Loxiol G70S, Henkel) | 0.4 |
| Process aid (Plastistrength 550, Arkema) | 1 |
| Antisticking process aid (Plastistrength 770, Arkema) | 0.7 |
| MBS impact modifier (Clearstrength 303H, Arkema) | 8 |
| Stabiliser (see list below) | 1.5 or 1.7 |

The same stabilisers Stab 1, Stab 2 and Stab 3 as defined above are tested. Stab 2 and 3 are used at 1.5 phr and Stab 1 at 1.7 phr to compare formulations at equal tin content.

The b* value in Hunter L*a*b* scale (b*, ASTM Standard E 313) is measured on each sample withdrawn and the results are reported in Table 2 below:

TABLE 2

| t (min.) | Stab 1 (according to the invention) | Stab 2 (comparative) | Stab 3 (comparative) |
|---|---|---|---|
| 2 | 7.5 | 8 | 7.7 |
| 3 | 8.1 | 9.4 | 9.1 |
| 4 | 8.8 | 11 | 10 |
| 5 | 8.6 | 12 | 11 |
| 6 | 9.3 | 13 | 11 |
| 7 | 8.9 | 14 | 11 |
| 8 | 10 | 14 | 12 |
| 9 | 10 | 15 | 12 |
| 10 | 11 | 17 | 14 |
| 12 | 13 | 20 | 16 |
| 15 | 17 | 41 | 30 |
| 20 | 40 | 65 | 61 |

As in previous Example A above, the results listed in Table 2 show the efficiency of the stabiliser containing mono-alkyltin compound of high purity as described in the present invention not only on the initial colour of the PVC formulation but also on the long term colorhold retention compared to formulations with a much higher di-alkyltin compound content, i.e. mixtures of mono- and di-alkyltin compounds as known in the art.

Example C

Comparative Study on Long Term Colorhold Retention of Thin- and Thick-PVC Films Used in Film Calendaring Production, Each Containing Mono-Alkyltin- and/or Di-Alkyltin Compounds Each PVC formulation used in example B containing a copolymer widely used in film calendering production is milled during 5 minutes at 180° C. (Collin two-roll mill with rolls brought to 180° C., rotational speeds of the two cylinders are respectively adjusted to 20 rpm and 24 rpm) to obtain a thin film of 0.5 mm thickness.

Measurement of colour is made, as well as on a thicker film obtained from the thin film pressed under a plate press at a temperature of 190° C., during 5 minutes. This thicker film is 4 mm thick and colour (b*) is recorded as described above.

The results are reported in Table 3 below:

TABLE 3

| B* value | Stab 1 (according to the invention) | Stab 2 (comparative) | Stab 3 (comparative) |
|---|---|---|---|
| Thin film (0.5 mm) | 7.8 | 9.6 | 8.3 |
| Thick film (4 mm) | 35 | 51 | 47 |

Early colour provided by very high purity mono octyl tin stabiliser is excellent compared to current technology also in thick films.

Example D

Comparative Haze Study of Thin- and Thick-PVC Films Used in Film Calendering Production, each Containing Monoalkyltin- or Dialkyltin Compounds The PVC formulation used in Example A widely used in film calendering production is milled during 5 minutes at 180° C. (Collin two-roll mill with rolls heated to 180° C., rotational speeds of the two cylinders respectively adjusted to 20 rpm and 24 rpm) to obtain a thin film of 0.5 mm thickness.

Measurement of optical properties such as haze in a PVC sample is made, on both thin and thicker film obtained from the thin film pressed under a plate press at a temperature of 190° C., during 5 minutes. This thicker film is 4 mm thick and haze is recorded.

The haze value is measured on a Hazemeter according to ASTM D1003 on each sample and the results are reported in Table 4 below:

TABLE 4

| Haze value (%) | Stab 1 (according to the invention) | Stab 2 (comparative) |
|---|---|---|
| Thin film (0.5 mm) | 0.76 | 0.74 |
| Thick film (4 mm) | 7.9 | 10 |

Very high purity mono-alkyltin stabiliser is able to decrease the haze and then gives to the finished film an excellent level of transparency.

Example E

Comparative Colour Study of PVC Films Containing a Monoalkyltin-Compound and an Organic Co-Stabiliser The advantageous use of a co-stabiliser together with a high purity mono-alkyltin stabiliser is illustrated: the formulation described below is evaluated using a Collin two-roll mill, the rolls of which are heated to 190° C. The rotational speeds of the two cylinders are respectively adjusted to 20 rpm and 24 rpm, providing sufficient friction to gelate PVC and sufficient heat to thoroughly study the thermal stabilisation efficiency of stabilisers.

The gap between the cylinders is adjusted to 0.5 mm. Samples are withdrawn from the cylinders at regular time intervals, their coloration being recorded.

The tested formulations are the following:

| | |
|---|---|
| PVC (Lacovyl RB8010, Arkema, kW = 57) | 100 |
| Epoxydised soybean oil (Ecepox PB3, Arkema) | 1 |
| Hydrogenated castor oil (Loxiol G15, Henkel) | 0.6 |
| Oxidized PE wax (A-C 316A, Honeywell) | 0.12 |
| Process aid (Plastistrength 551, Arkema) | 0.6 |
| Antisticking process aid (Plastistrength 770, Arkema) | 1 |
| MBS impact modifier (Clearstrength 320, Arkema) | 8 |
| Stab 1 | 1.3 |
| Dihydro-1,4-dimethyl-2,6 dicarbododecyloxy-3,5-pyridine ('DHP'; CAS 36265-41-5; Stavinor ® D507, Arkema) | 0 to 0.2 |

The b* value in Hunter L*a*b* scale (b*, ASTM Standard E 313) is measured on each sample withdrawn and the results are reported in Table 5 below:

TABLE 5

| T (min.) | Stab 1 | Stab 1 + 0.05 phr DHP | Stab 1 + 0.1 phr DHP |
|---|---|---|---|
| 2 | 7.4 | 7.1 | 7.1 |
| 4 | 8.3 | 7.8 | 7.8 |
| 6 | 9.1 | 8.4 | 7.9 |
| 8 | 10 | 9.1 | 8.2 |
| 10 | 11 | 10.1 | 9.1 |
| 12 | 12.9 | 12 | 10.6 |
| 14 | 14.7 | 13.7 | 11.7 |
| 16 | 17.3 | 16.5 | 14.1 |
| 18 | 20.3 | 23.8 | 17.5 |
| 20 | 26.9 | 28 | 17.6 |

It is well known that dihydropyridine-based compounds alone, such as DHP alone, give poor results in this test. However, when combined with a highly pure mono-alkyltin stabiliser according to the invention, the co-stabilising effect is drastically improved in terms of initial colour and colour hold during a dynamic thermal stability test.

This is the evidence of a synergistic effect resulting from the use of dihydropyridine-based compounds together with high purity mono-alkyltin compounds.

A good effect of initial colour may also be evidenced by preparing first a film on two roll mill (190° C., 5 minutes) and then pressing several sheets until a thickness of 4 mm (plate press at 190° C. during 10 minutes with pressure: 30 bars, during 60 sec., 200 bars during 40 sec., 300 bars during 180 sec.). Yellow index (YI) and L* value in Hunter L*a*b* scale (b*, ASTM Standard E 313) is given in table 6 below:

TABLE 6

| | Stab 1 | Stab 1 + 0.05 phr DHP | Stab 1 + 0.1 phr DHP | Stab 1 + 0.2 phr DHP |
|---|---|---|---|---|
| YI | 35.5 | 27.7 | 25.5 | 24 |
| L* | 79.3 | 81.3 | 82.1 | 81.6 |

Yellow index decreases with adding a dihydropyridine-based compound with the composition of the invention (highly pure mono-alklytin compound) and L* value increases attesting a higher whiteness.

Example F

Comparative Colour Study of PVC Films Containing a Monoalkyltin-Compound and Another Organic Co-Stabiliser Based on Dissodium Adipate The advantageous use of another co-stabiliser together with a high purity mono-alkyltin stabiliser is illustrated: the formulation described below is evaluated using a Collin two-roll mill, the rolls of which are heated to 195° C. The rotational speeds of the two cylinders are respectively adjusted to 20 rpm and 24 rpm, providing sufficient friction to gelate PVC and sufficient heat to thoroughly study the thermal stabilisation efficiency of stabilisers.

The gap between the cylinders is adjusted to 0.5 mm. Samples are withdrawn from the cylinders at regular time intervals, their coloration being recorded.

The tested formulations are the following:

| | |
|---|---|
| PVC (Lacovyl SO71, Arkema, kW = 57) | 100 |
| Epoxydised soybean oil (Ecepox PB3, Arkema) | 1 |
| Oxidized PE wax (A-C 316A, Honeywell) | 0.12 |
| Process aid (Plastistrength 551, Arkema) | 1.2 |
| Antisticking process aid (Plastistrength 770, Arkema) | 1 |
| MBS impact modifier (Clearstrength 303H, Arkema) | 8 |
| Glycerol monostearate (Loxiol G12, Henkel) | 1.2 |
| Adipate stearate pentaerythritol (Loxiol G70S, Henkel) | 1.2 |
| Stab 1 | 1.1 to 1.4 |
| Disodium adipate ('DSA', Reapak NAD) | 0 to 0.4 |

The b* value in Hunter L*a*b* scale (b*, ASTM Standard E 313) is measured on each sample withdrawn and the results are reported in Table 7 below:

TABLE 7

| T (min.) | Stab 1 1.1 phr | Stab 1 1.4 phr | Stab 1 1.1 phr + DSA 0.4 phr |
|---|---|---|---|
| 2 | 13.5 | 13.2 | 15.2 |
| 4 | 14.5 | 14.0 | 15.2 |
| 6 | 16.2 | 14.8 | 18.8 |
| 8 | 18.9 | 16.1 | 21.6 |
| 10 | 24.2 | 18.4 | 24.2 |
| 12 | 34.3 | 22.2 | 28 |
| 14 | 49.1 | 26.5 | 31.6 |
| 16 | 70.9 | 35.6 | 37.1 |
| 18 | 88.5 | 49.4 | 43.7 |
| 20 | 101 | 68.3 | 50.5 |
| 22 | 107 | 82.4 | 51.7 |
| 24 | | 96.6 | 57.9 |

Disodium adipate when combined with a highly pure mono-alkyltin stabiliser according to the invention improves the co-stabilising effect especially in terms of colour hold during a dynamic thermal stability test.

This is the evidence of a synergistic effect resulting from the use of disodium adipate together with high purity mono-alkyltin compounds.

Part 3

Reproduction/Developmental Toxicity Study(According to OECD 421 Guideline)

Example AA

14-Day Oral (Diet) Dose-Range Toxicity Study (Preliminary Study for the Reproduction/Developmental Study)

The aim of this study is to select appropriate dose-levels for the main study.
Materials and Methods:
Groups: one control group and four test groups (4 males and 4 female per group) administered with different dose levels of the test substance;

Housing: 2 rats/sex/cage, macrolon cages;
Species: rat, Wistar outbred, Charles River Wiga GmbH, 9-10 weeks of age at start;
Carrier: Commercial rodent diet (Rat & Mouse No. 3 Breeding diet, RM3), ad libitum;
Treatment: Administration via the diet during 14 consecutive days; one batch of test diets is prepared shortly before initiation of treatment and stored in a freezer/refrigerator; the feed in the animal feeders is refreshed twice per week;
Clinical observations: general observations (all rats): daily; morbidity is checked again in the afternoon;
Body weight: at least once pretest, twice per week from the start of treatment (for the last time, on the day of scheduled necropsy);
Food consumption: twice weekly per cage (2 rats/cage) from the start of treatment;
Water consumption: visual inspection of the drinking bottles;
Pathology:
  macroscopic examination (all rats);
  weighing the following organs of all the surviving rats: kidneys, liver, spleen, testes, thymus;
  preservation: the weighed organs are preserved in formalin and discarded when the results of the subsequent 90-day study indicate non need for microscopy on tissues from the 14-day study;

On each day of analysis, calibration solutions are prepared by spiking rodent diet with a stock solution of the organotin compound followed by derivatisation with sodium tetraethyl borate, in order to derivatise the octyltin compounds to the corresponding octyltin-ethyl compounds, with simultaneous extraction of the derivatised compounds into hexane.

The concentration of the test substance in diet is then determined by GC-MS of the hexane extracts.

Example AB

Reproduction/Developmental Toxicity Screening Test (According to OECD 421 Guideline)

The objective of this study is to assess whether octyltin tris (2-ethylexylmercaptoacetate) causes adverse effects on reproduction and/or development of wistar rats. This study was preceded by a dose-range finding study (see Example AA).

Materials and Methods:
Groups: one control group and three test groups (12 males and 12 female per group) administered with different dose levels of the test substance;
Housing: Pre-mating (PM): 4 rats/sex/cage, macrolon cages;
  Mating (M): 1 male and 1 female per cage;
  Gestation (G) and lactation: 1 rat/sex/cage, macrolon cages;
Species: rat, Wistar outbred, Charles River Wiga GmbH, 9-10 weeks of age at start;
Carrier: Commercial rodent diet (Rat & Mouse No. 3 Breeding diet, RM3), ad libitum;
Treatment: Administration via the diet during 14 consecutive days premating; during 14 consecutive days mating, gestation and lactation up to 4 days (males are given the test substance in the diet until sacrifice at the end of the mating period);
  one or two batches of test diets are prepared shortly before initiation of treatment and stored in a freezer/refrigerator; the feed in the animal feeders is refreshed once per week;
Clinical observations: general clinical observations (all rats): daily; morbidity is checked again in the afternoon;
Body weight: at least once pretest, males and females, premating and mating weekly;
Food consumption: males and females, premating and mating weekly; for female during gestation: GD 0, 7, 14 and 21 during lactation; PN 1 and 4;
Pups: sex, body, weight, number of live and dead pups, clinical signs PN 1 and 4;
Water consumption: visual inspection of the drinking bottles;
Pathology:
  macroscopic examination (all rats);
  count: number of implantations (uterus) and corpora lutea (ovaria);
  weighing the following organs of all the surviving rats: testes (males), epididymes (females), thymus;
  preservation all animals): testes, epididymes, seminal vesicles, prostate, ovaries, uterus, thymus and organs and tissues showing macroscopic abnormalities; the organs are preserved in formalin and discarded when the results of the OECD 421 study indicate non need for microscopy;
Histopathology: preserved tissues for control and high level only (low and mid dose groups only).

On each day of analysis, calibration solutions are prepared by spiking rodent diet with a stock solution of the organotin compound followed by derivatisation with sodium tetraethyl borate, in order to derivatise the octyltin compounds to the corresponding octyltin-ethyl compounds, with simultaneous extraction of the derivatised compounds into hexane.

The concentration of the test substance in diet is then determined by GC-MS of the hexane extracts.

Results of the Toxicity Tests of Examples AA and AB

In the preliminary study (example AA), no clinical abnormalities were observed as well as no change in body weight and food consumption. Furthermore no abnormalities were observed at necropsy and no effects were observed on organ weights In the main reproduction and developmental toxicity screening study in rats (example AB), the oral administration of octyltin tris (2-ethylexylmercaptoacetate) at 200, 500 and 1250 mg/kg diet was well tolerated at all dose-levels. No effects were observed on reproduction organs or on pre- and post-natal development. The no averse effect level (NOAEL) for parental toxicity, fertility and development is 1250 mg/kg diet (approximately 72 and 96 mg octyltin tris (2-ethylexylmercaptoacetate)/kg body weight/day for male and female animals respectively.

The results of these new studies with high purity monooctyltin compound as defined above in Examples AA and AB indicate that the composition of the present invention that contains a high amount of mono-alkyltin compounds has no target organ effects and particularly no effects on fertility and reproduction. These results on the pure monooctyltin are different for the available published results performed on mixture on mono- and dialkyltin compounds, which have shown severe effects on fertility and reproduction. Mono-alkyltin compounds of high purity are much less toxic than compositions comprising less pure mono-alkyltin compounds, and particularly the known compositions containing both mono- and di-alkyltin compounds in almost or substantially almost comparable content.

The invention claimed is:

1. Composition comprising:
   from 85 wt % to 99.999 wt % of at least one monoalkyltin compound of formula $RSn(T)_3$;
   from 0.001 wt % to 10 wt % of at least one di-alkyltin compound of formula $R_2Sn(T)_2$;
   from 0.001 wt % to 5 wt % of at least one tri-alkyltin compound of formula $R_3Sn(T)$; and
   from 0 wt % to 5 wt % of one or more impurities,
   wherein R is linear, branched or cyclic $C_1$-$C_{20}$ alkyl and T is a ligand selected from the group consisting of thioglycolate esters, 2-ethylhexylthioglycolate esters, iso-octylthioglycolates, iso-butylthioglycolates, thioglycolate, hydroxyl, carboxylates, maleates, diketonates, alcoholates, and 2-ethylhexylmercaptoacetate.

2. Composition according to claim 1, wherein the weight ratio of (mono-alkyltin compound)/(di-alkyltin compound) is not less than 90/10.

3. Composition according to claim 1, wherein the weight ratio of (mono-alkyltin compound)/(di-alkyltin compound) is not less than 99/1.

4. Composition according to claim 1, wherein R is selected from the group consisting of methyl, ethyl, n-propyl, iso-propyl, n-butyl, iso-butyl, n-pentyl, n-hexyl, n-heptyl, n-octyl, 2-ethylhexyl, iso-octyl, and decyl.

5. Composition according to claim 1, wherein $RSn(T)_3$ is $RSn[tris(2-ethylhexylmercaptoacetate)]$.

6. Composition according to claim 5, wherein $RSn(T)_3$ is selected from the group consisting of monomethyltin[tris(2-ethylhexylmercaptoacetate)], mono-n-butyltin[tris(2-ethylhexyl-mercaptoacetate)], mono-n-octyl[tris(2-ethylhexylmercaptoacetate)], and mixtures thereof.

7. Composition according to claim 1 further comprising at least one co-stabiliser and/or at least one additive.

8. Composition according to claim 7, wherein the co-stabiliser is selected from the group consisting of epoxydised soy bean oil, dihydropyridine-based compounds, α-phenylindole, polyols, disaccharide alcohols, perchlorate-based compounds, glycidyl compounds, layered lattice compounds, zeolite compounds, phosphite compounds, β-diketones, β-ketoesters, mercaptocarboxylic esters, metal soaps, amino-and/or thiouracils, hydrazides, and mixtures thereof.

9. Composition according to claim 7, further comprising at least one dihydropyridine-based compound, and optionally at least one perchlorate compound.

10. Composition according to claim 7, wherein the additive is from the group consisting of stabilisers, auxiliaries and processing aids, lubricants, plasticizers, pigments, fillers, epoxidized fatty acid esters, antioxidants, UV absorbers and light stabilisers, optical brighteners, impact modifiers, gelling agents, antistats, biocides, metal passivators, flame retardants, blowing agents, antifog agents, compatibilisers and anti plate-out agents, and mixtures thereof.

11. Composition comprising a chlorine-containing polymer and a composition comprising:
    from 85 wt % to 99.999 wt % of at least one monoalkyltin compound of formula $RSn(T)_3$;
    from 0.001 wt % to 10 wt % of at least one di-alkyltin compound of formula $R_2Sn(T)_2$;
    from 0.001 wt % to 5 wt % of at least one tri-alkyltin compound of formula $R_3Sn(T)$; from 0 wt % to 5 wt % of one or more impurities; and optionally at least one co-stabiliser and/or one or more additive(s), wherein R is linear, branched or cyclic $C_1$-$C_{20}$ alkyl and T is a ligand selected from the group consisting of thioglycolate esters, 2-ethylhexylthioglycolate esters, iso-octylthioglycolates, iso-butylthioglycolates, thioglycolate, hydroxyl, carboxylates, maleates, diketonates, alcoholates, and 2-ethylhexylmercaptoacetate.

12. Article comprising at least one polymer matrix and a composition comprising: from 85 wt % to 99.999 wt % of at least one monoalkyltin compound of formula $RSn(T)_3$; from 0.001 wt % to 10 wt % of at least one di-alkyltin compound of formula $R_2Sn(T)_2$; from 0.001 wt % to 5 wt % of at least one tri-alkyltin compound of formula $R_3Sn(T)$; from 0 wt % to 5 wt % of one or more impurities; and
    optionally one or more additive(s) and/or co-stabiliser(s), wherein R is linear, branched or cyclic $C_1$-$C_{20}$ alkyl and T is a ligand selected from the group consisting of thioglycolate esters, 2-ethylhexylthioglycolate esters, iso-octylthioglycolates, iso-butylthioglycolates, thioglycolate, hydroxyl, carboxylates, maleates, diketonates, alcoholates, and 2-ethylhexylmercaptoacetate.

13. Article according to claim 12, wherein the matrix is a chlorine-containing polymer.

14. Process of preparation of a composition comprising: from 85 wt % to 99.999 wt % of at least one monoalkyltin compound of formula $RSn(T)_3$; from 0.001 wt % to 10 wt % of at least one di-alkyltin compound of formula $R_2Sn(T)_2$; from 0.001 wt % to 5 wt % of at least one tri-alkyltin compound of formula $R_3Sn(T)$; and from 0 wt % to 5 wt % of one or more impurities, wherein R is linear, branched or cyclic $C_1$-$C_{20}$ alkyl and T is a ligand selected from the group consisting of thioglycolate esters, 2-ethylhexylthioglcolate esters, iso-octglthioglycolates, iso-butylthioglycolates, thioglycolate, hydroxyl, carboxylates, maleates, diketonates, alcoholates, and 2-ethylhexylmercaptoacetate, the process comprising:
    α) hydrostannylating a 1-alkene to the corresponding mono-alkyltin trihalide $RSn(Hal)_3$ in the presence of a transition metal catalyst, tin(II) dihalide and hydrogen halide; and
    β) converting the mono-alkyltin trihalide $RSn(Hal)_3$ to $RSn(T)_3$ by contacting the mono-alkyltin trihalide $RSn(Hal)_3$ with a compound of formula H-T in the presence of a suitable base or, alternatively, converting $RSn(Hal)_3$ to alkylstannoic acid of formula $RSn(O)OH$ using a hydroxide base followed by contacting the alkylstannoic acid with a compound of formula H-T under elimination of water.

15. Process according to claim 14, wherein said stannous halide is $SnCl_2$ and said hydrogen halide is HCl.

16. Process according to claim 14, wherein R is selected from the group consisting of methyl, n-butyl, iso-octyl and n-octyl.

17. Process according to claim 14, wherein T is selected from the group consisting of 2-ethyl hexyl mercaptoacetate and hydroxyl.

18. Process of preparation of a composition comprising: from 85 wt % to 99.999 wt % of at least one monoalkyltin compound of formula $RSn(T)_3$; from 0.001 wt % to 10 wt % of at least one di-alkyltin compound of formula $R_2Sn(T)_2$; from 0.001 wt % to 5 wt % of at least one tri-alkyltin compound of formula $R_3Sn(T)$; and from 0 wt % to 5 wt % of one or more impurities, wherein R is linear, branched or cyclic $C_1$-$C_{20}$ alkyl and T is a ligand selected from the group consisting of thioglycolate esters, 2-ethylhexylthioglycolate esters, iso-octylthioglycolates, iso-butylthioglycolates, thioglycolate, hydroxyl, carboxylates, maleates, diketonates, alcoholates, and 2-ethylhexylmercaptoacetate, the process comprising the steps of:

a) preparing a solution of stannous halide $SnHal_2$ in a solvent, together with a transition metal-based catalyst;
b) reacting the obtained solution with a molar excess of an alkene or cycloalkene precursor of the R radical, at a temperature ranging between room temperature to 200° C. in the presence of hydrogen halide (H-Hal) and optionally metallic tin (Sn);
c) optionally removing the solvent of the reaction medium, by stripping or vacuum-distillation of the solvent;
d) optionally filtering the crude reaction medium;
e) adding a 2- to 5-fold molar excess (relative to the obtained monoalkyltin trihalide) of H-T and water under stirring;
f) neutralising the reaction medium with alkali or alkaline-earth hydroxide, and forming a water layer and an organic layer;
g) separating the water layer from the organic layer; and
h) removing the solvent from the organic layer, and optionally filtering to recover $RSn(T)_3$ of high purity.

19. Process according to any of claim 18, wherein R is selected from the group consisting of methyl, n-butyl, iso-octyl and n-octyl.

20. Process according to claim 18, wherein T is selected from the group consisting of 2-ethylhexyl mercaptoacetate and OH.

* * * * *